US008586746B2

(12) United States Patent
Schrimpf et al.

(10) Patent No.: US 8,586,746 B2
(45) Date of Patent: Nov. 19, 2013

(54) AMINO-AZA-ADAMANTANE DERIVATIVES AND METHODS OF USE

(75) Inventors: Michael R. Schrimpf, Grayslake, IL (US); Kevin B. Sippy, Antioch, IL (US); David J. Anderson, Lake Bluff, IL (US); William H. Bunnelle, Mundelein, IL (US); Diana L. Nersesian, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 200 days.

(21) Appl. No.: 13/012,130

(22) Filed: Jan. 24, 2011

(65) Prior Publication Data

US 2011/0118301 A1 May 19, 2011

Related U.S. Application Data

(62) Division of application No. 11/517,064, filed on Sep. 7, 2006, now Pat. No. 7,897,766.

(60) Provisional application No. 60/720,326, filed on Sep. 23, 2005.

(51) Int. Cl.
C07D 221/22 (2006.01)
C07D 221/06 (2006.01)

(52) U.S. Cl.
USPC ............................................ 546/79; 546/133

(58) Field of Classification Search
USPC .................................................. 546/79, 133
See application file for complete search history.

(56) References Cited

U.S. PATENT DOCUMENTS

| 4,816,453 | A | 3/1989 | Watts |
| 4,950,759 | A | 8/1990 | van Wijngaarden et al. |
| 4,985,424 | A | 1/1991 | van Wijngaarden et al. |
| 5,208,028 | A | 5/1993 | Clement et al. |
| 5,260,303 | A | 11/1993 | Becker et al. |
| 5,280,028 | A | 1/1994 | Flynn et al. |
| 5,399,562 | A | 3/1995 | Becker et al. |
| 5,434,151 | A | 7/1995 | Cai et al. |
| 5,591,749 | A | 1/1997 | Becker et al. |
| 5,604,239 | A | 2/1997 | Becker et al. |
| 5,643,917 | A | 7/1997 | Flynn et al. |
| 5,723,472 | A | 3/1998 | Miyazawa et al. |
| 5,840,903 | A | 11/1998 | Flynn et al. |
| 5,952,339 | A | 9/1999 | Bencherif et al. |
| 5,986,100 | A | 11/1999 | Crooks et al. |
| 6,057,446 | A | 5/2000 | Crooks et al. |
| 6,093,724 | A | 7/2000 | Grewal et al. |
| 6,251,916 | B1 | 6/2001 | Grewal et al. |
| 6,323,194 | B1 | 11/2001 | Grewal et al. |
| 6,417,359 | B1 | 7/2002 | Crooks et al. |
| 6,423,842 | B1 | 7/2002 | Grewal et al. |
| 6,555,550 | B1 | 4/2003 | Grewal et al. |
| 6,627,648 | B1 | 9/2003 | Dull et al. |
| 2005/0065178 | A1 | 3/2005 | Basha et al. |
| 2005/0101602 | A1 | 5/2005 | Basha et al. |

FOREIGN PATENT DOCUMENTS

| EP | 227215 A1 | 7/1987 |
| EP | 645391 A2 | 3/1995 |
| FR | 2543954 | 4/1983 |
| WO | WO9215593 A1 | 9/1992 |
| WO | WO9400454 A1 | 1/1994 |
| WO | WO9402482 A1 | 2/1994 |
| WO | WO9951601 A1 | 10/1999 |
| WO | WO9951602 A1 | 10/1999 |
| WO | WO0011001 A1 | 3/2000 |
| WO | WO0071520 A2 | 11/2000 |
| WO | WO0202564 A1 | 1/2002 |
| WO | WO03094831 A2 | 11/2003 |
| WO | WO2005028477 A1 | 3/2005 |

OTHER PUBLICATIONS

Dorwald F. A. Side Reactions in Organic Synthesis, 2005, Wiley: VCH, Weinheim p. IX of Preface.*
Adams C.E. et al., "Development of the a7 nicotinic cholinergic receptor in rat hippocampal formation," Developmental Brain Research, 2002, vol. 139 (2), pp. 175-187.
Adler L.E., et al., "Schizophrenia, Sensory Gating, and Nicotinic Receptors," Schizophrenia Bulletin, 1998, vol. 24 (2), pp. 189-202.
Becker D.P., et al., "A Short Synthesis of 1-Azaadamantan-4-One and the 4r and 4s Isomers of 4-Amino-1-Azaadamantane," Synthesis, 1992, vol. 11, pp. 1080-1082.
Cordero-Erausquin M., et al., "Tonic Nicotinic Modulation of Serotoninergic Transmission in the Spinal Cord," Proceedings of the National Academy of Sciences , 2001, vol. 98 (5), pp. 2803-2807.
Cross L.C., et al., "IUPAC Commission on Nomenclature of Organic Chemistry: Rules for the Nomenclature of Organic Chemistry, Section E: Stereochemistry ," Pure and Applied Chemistry, 1976, vol. 45, pp. 13-30.
Dorwald F.Z., "Side Reactions in Organic Synthesis—a Guid to Successful Synthesis Design," 2005, pp. 9-16.
Falk L., et al., "Higher Expression of .Alpha.7 Nicotinic Acetylcholine Receptors in Human Fetal Compared to Adult Brain," Developmental Brian Research, 2003, vol. 142 (2), pp. 151-160.
Flynn D.L., et al., "New Aza(NOR)Adamantanes are Agonists at the Newly Identified Serotonin 5-Ht4 Receptor and Antagonists at the 5-HT3 Receptor," Bioorganic & Medicinal Chemistry Letters , 1992, vol. 2 (12), pp. 1613-1618.
Friedman J.I., et al., "A Double Blind Placebo Controlled Trial of Donepezil Adjunctive Treatment to Risperidonc for the Cognitive Impairment of Schizophrenia," Biological Psychiatry , 2002, vol. 51, pp. 349-357.

(Continued)

Primary Examiner — Rita Desai
(74) Attorney, Agent, or Firm — Lisa V. Mueller; Michael Best & Friedrich LLP

(57) ABSTRACT

The invention relates to amine-substituted aza-adamantane derivatives, compositions comprising such compounds, and methods of treating conditions and disorders using such compounds and compositions.

Radiolabelled compounds useful for evaluating the binding affinity to α7 nicotinic acetylcholine receptors also are described.

7 Claims, No Drawings

(56) References Cited

OTHER PUBLICATIONS

Furniss B.S., et al., Vogel's Textbook of Practical Organic Chemistry, 5th Edition, Longman Scientific & Technical, 1989, Table of Contents.

Greene T.W., et al., "Protection for the Amino group," Protective Groups in Organic Synthesis, 1999, Third Edition, pp. 494-653.

Heeschen C., et al., "A Novel Angiogenic Pathway Mediated by Non-Neuronal Nicotinic Acetycholine Receptors," Journal of Clinical Investigation, 2002, vol. 110 (4), pp. 527-536.

Heeschen C., et al., "Nicotine Stimulates Angiogenesis and Promotes Tumor Growth and Athcrsclerosis," Nature Medicine, 2001, vol. 7 (7), pp. 833-839.

Hiebl J., et al., "New Synthesis of Isoquinoline-3-Carboxylates," Tetrahedron Letters, 1999, vol. 40, pp. 7935-7938.

Higuchi T., et al., "The Chemistry of a Novel 5,5-Diphenylhydantoin Pro-drug," A.C.S. Symposium Series, vol. 14, pp. 154-183.

Iriepa I., et al., "Synthesis and Structure Study of a Series of Amides Derived from 4alpha- and 4beta-Amino-1-Azaadamantanes as Potential 5-HT3 Receptor Antagonists," Journal of Molecular Structure, 1999, vol. 509, pp. 105-114.

Jacobi J., et al., "Nicotine Accelerates Angiogenesis and would Healing in Genetically Diabetic Mice," American Journal of Pathology, 2002, vol. 161 (1), pp. 97-104.

Jonnala R.R., et al., "Relationship between the Increased Cell Surface .alpha.7 nicotinic Receptor Expression and Neuroprotection Induced by Several Nicotinic Receptor Agonists," Journal of Neuroscience Research, 2001, vol. 66 (4), pp. 565-572.

Kihara T., et al., "Alpha.7 Nicotinic Receptor Transduces Signals to Phosphatidylinositol 3-kinase to Block A .beta.-amyloid-induced Neurotoxicity," Journal of Biological Chemistry, 2001, vol. 276 (17), pp. 13541-13546.

Leonard S., et al., "Smoking and Schizophrenia: Abnormal Nicotinic Receptor Expression," European Journal of Pharmacology, 2000, vol. 393 (1-3), pp. 237-242.

Levin E.D., "Nicotinic Receptor Subtypes and Cognitive Function," Journal of Neurobiology, 2002, vol. 53 (4), pp. 633-640.

Liu Q.S., et al., "Alpha-Amyloid Peptide Blocks the Response of Alpha.7-Containing Nicotinic Receptors on Hippocampal Neurons," Proceedings of the National Academy of Sciences, 2001, vol. 98 (8), pp. 4734-4739.

Poste G., et al., "Lipid Vesicles as Carriers for Introducing Biologically Active Materials into Cells," Methods in Cell Biology, 1976, vol. 14, pp. 33-71.

Roche E.B., ed., Bioreversible Carries in Drug Design Theory and Application, Pergamon Press, 1987, Table of Contents.

Rowley M., et al., "Current and Novel Approaches to the Drug Treatment of Schizophrenia," Journal of Medicinal Chemistry, 2001, vol. 44 (4), pp. 477-501.

Sawa A., et al., "Schizophrenia: Neural Mechanisms for Novel Therapies," Molecular Medicine, 2003, vol. 9 (1-2), pp. 3-9.

Schildan A., et al., ""Synthesis and Evaluation of Tritium Labelled 10- methylgalanthamine Iodide: A Novel Compound to Examine the Mechanism of Interaction of Galanthamine Derivatives with the Nicotinic Acetylcholine Receptors,"" Journal of Labelled Compounds and Radiopharmaceuticals, 2003, vol. 46 (12), pp. 1117-1125.

Shimohama S.,et al., "Nicotinic Alpha 7 Receptors Protect Against Glutamate Neurotoxicity and Neuronal Ischemic Damage," Brain Research, 1998, vol. 779 (1-2), pp. 359-363.

Son J.H., et al., "Evidence Suggesting that the Mouse Sperm Acrosome Reaction Initiated by the Zona Pellucida Involves An . Alpha.7 Nicotinic Acetylcholine Receptor," Biology of Reproduction, 2003, vol. 68 (4), pp. 1348-1351.

Stevens K.E., et al., "Selective A7-Nicotinic Agonists Normalize Inhibition of Auditory Response in Dba Mice," Psychopharmacology, 1998, vol. 136 (4), pp. 320-327.

Tsuneki H. et al., "Mouse Muscle Denervation Increases Expression of an A7 Nicotinic Receptor with Unusual Pharmacology," Journal of Physiology, 2003, vol. 547 (1), pp. 169-179.

Wang H., et al., "Nicotinic Acetylcholine Receptor Alpha7 Subunit is an Essential Regulator of Inflammation," Nature, 2003, vol. 421 (6921), pp. 384-388.

\* cited by examiner

AMINO-AZA-ADAMANTANE DERIVATIVES AND METHODS OF USE

This application is a division of U.S. patent application Ser. No. 11/517,064, filed on Sep. 7, 2006, which claims priority from U.S. Patent Application No. 60/720,326, filed Sep. 23, 2005, each of which is herein incorporated by reference in its entirety.

BACKGROUND OF THE INVENTION

1. Technical Field

The invention relates to amine-substituted aza-adamantane derivatives, compositions comprising such compounds, and methods of treating conditions and disorders using such compounds and compositions.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function.

Typically, nAChRs are ion channels that are constructed from a pentameric assembly of subunit proteins. At least 12 subunit proteins, α2-α10 and β2-β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the α4β2 subtype), while another major population of receptors is comprised of homomeric $(\alpha 7)_5$ (the α7 subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The α7 nAChRs have been shown to play a significant role in enhancing cognitive function, including aspects of learning, memory and attention (Levin, E. D., J. Neurobiol. 53: 633-640, 2002). For example, α7 nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities.

The activity at the α7 nAChRs can be modified or regulated by the administration of α7 nAChR ligands. The ligands can exhibit antagonist, agonist, or partial agonist properties. Thus, α7 ligands have potential in treatment of various cognitive disorders.

Although compounds demonstrating activity at the α7 nAChRs are known, it would be beneficial to provide compounds that interact selectively with α7-containing neuronal nAChRs compared to other subtypes.

SUMMARY OF THE INVENTION

The invention is directed to amino-aza-adamantane containing compounds as well as compositions comprising such compounds, and method of using the same.

One aspect of the present invention is directed toward a compound of formula (I)

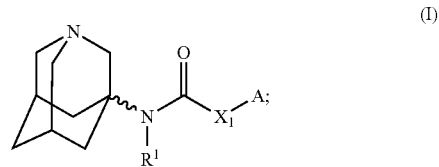

or a pharmaceutically suitable salt or prodrug thereof, wherein $X_1$ is a bond or is selected from —O—, —O-alkyl, —NR²— and —NR²-alkyl, wherein the oxygen atom of —O-alkyl and the nitrogen atom of —NR²-alkyl is attached to the parent molecular moiety;

A is selected from $Ar^1$, —$Ar^2$—Y—$Ar^3$ and $Ar^4$;

$Ar^1$ is aryl, provided that if $Ar^1$ is a phenyl ring containing a meta-substituted halogen group, then the phenyl can not be substituted with both methoxy and —$NH_2$;

$Ar^2$ is selected from the aryl and heteroaryl;

$Ar^3$ is selected from aryl and heteroaryl;

$Ar^4$ is selected from heteroaryl and heterocycle, provided that $Ar^4$ is not benzimidazolyl, 2,3-dihydro-1H-indolyl or imidazole[1,2-a]pyridine;

Y is a bond or is selected from —O—, —S— and —NR³—; and $R^1$, $R^2$ and $R^3$ are individually selected from hydrogen and $C_1$-$C_6$ alkyl;

with the provision that the compound is not selected from the group consisting of N-(1-aza-tricyclo[3.3.1.1³,⁷]dec-4-yl)-benzamide;

N-(1-aza-tricyclo[3.3.1.1³,⁷]dec-4-yl)-3,5-dichloro-benzamide;

N-(1-aza-tricyclo[3.3.1.1³,⁷]dec-4-yl)-2-methoxy-benzamide;

1-H-indole-3-carboxylic acid (1-aza-tricyclo[3.3.1.1³,⁷]dec-4-yl)-amide;

(4α,β)-4-amino-N-[1-azaadamantan-4-yl]-5-chloro-2-methoxy benzamide;

6-chloro-imidazo[1,2-a}pyridine-8-carboxylic acid (1-aza-tricyclo[3.3.1.1³,⁷]dec-4-yl)amide; and 3-ethyl-indolizine-1-carboxylic acid (1-aza-tricyclo[3.3.1.1³,⁷]dec-4-yl)-amide.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating nAChR activity, for example α7 nAChR activity. The method is useful for treating, preventing or both treating and preventing conditions and disorders related to α7 nAChR activity in mammals. More particularly, the method is useful for conditions and disorders related to attention deficit disorder, attention deficit hyperactivity disorder (ADHD), Alzheimer's disease (AD), mild cognitive impairment, age-associated memory impairment (AAMI), senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

Radiolabelled compounds useful for evaluating the binding affinity of compounds, for example amine-substituted aza-adamantane derivatives, to α7 nicotinic acetylcholine receptors also are described herein.

The compounds, compositions comprising the compounds, and methods for treating or preventing conditions and disorders by administering the compounds are further described herein.

DETAILED DESCRIPTION OF THE INVENTION

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, and —C≡CCH(CH$_3$)CH$_2$—.

The term "alkynyloxy" as used herein, means an alkynyl group, as defined herein, appended to the parent molecular moiety through an oxygen atom. Representative examples of alkynyloxy include, but are not limited to, 2-propynyloxy and 2-butynyloxy.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, —NZ$_1$Z$_2$, and (NZ$_3$Z$_4$)carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "azido" as used herein, means a —N$_3$ group.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1] heptane, bicyclo[2.2.1]heptane, bicyclo[2.2.2]octane, bicyclo[3.2.2]nonane, bicyclo[3.3.1]nonane, and bicyclo[4.2.1] nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the present invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$_1$Z$_2$, and (NZ$_3$Z$_4$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring contains two double bonds and one, two, three or four nitrogen atoms and optionally one oxygen or sulfur atom. The 6 membered ring contains three double bonds and one, two, three or four nitrogen atoms. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl.

The heteroaryl groups of the present invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$_1$Z$_2$ and (NZ$_3$Z$_4$)carbonyl. Heteroaryl groups of the present invention that are substituted may be present as tautomers. The present invention encompasses all tautomers including non-aromatic tautomers.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)

methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" as used herein, means a heteroarylalkyl, as defined herein, appended to the parent molecular moiety through a carbonyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio, and thien-3-ylmethylthio.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" as used herein, means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ_1Z_2$ and ($NZ_3Z_4$)carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkyl" as used herein, means a heterocycle, as defined herein, appended to the parent molecular moiety through an alkyl group, as defined herein. Representative examples of heterocyclealkyl include, but are not limited to, The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-1-pyrrolidin-1-yl-butylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" as used herein, means a heterocyclealkyl group, as defined herein, appended to the parent molecular moiety through a sulfur atom. Representative examples of heterocyclealkylthio include, but are not limited to, 2-pyridin-3-ylethylthio, 3-quinolin-3-ylpropythio, and 5-pyridin-4-ylpentylthio.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" as used herein, means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, isopropyl, n-butyl, iso-butyl, sec-butyl, and tert-butyl.

The term "lower alkylthio" as used herein, is a subset of alkylthio, means a lower alkyl group, as defined herein, appended to the parent molecular moiety through a sulfur atom. Representative examples of lower alkylthio include, but are not limited, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NZ$_1$Z$_2$" as used herein, means two groups, Z$_1$ and Z$_2$, which are appended to the parent molecular moiety through a nitrogen atom. Z$_1$ and Z$_2$ are each independently selected from the group consisting of hydrogen, alkyl, alkylcarbonyl, alkoxycarbonyl, aryl, arylalkyl, formyl and ($NZ_5Z_6$)carbonyl. In certain instances within the present invention, $Z_1$ and $Z_2$ taken together with the nitrogen atom to which they are attached form a heterocyclic ring. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "$NZ_3Z_4$" as used herein, means two groups, $Z_3$ and $Z_4$, which are appended to the parent molecular moiety through a nitrogen atom. $Z_3$ and $Z_4$ are each independently selected from the group consisting of hydrogen, alkyl, aryl and arylalkyl. Representative examples of $NZ_3Z_4$ include, but are not limited to, amino, methylamino, phenylamino and benzylamino.

The term "$NZ_5Z_6$" as used herein, means two groups, $Z_5$ and $Z_6$, which are appended to the parent molecular moiety through a nitrogen atom. $Z_5$ and $Z_6$ are each independently selected from the group consisting of hydrogen, alkyl, aryl and arylalkyl. Representative examples of $NZ_5Z_6$ include, but are not limited to, amino, methylamino, phenylamino and benzylamino.

The term "($NZ_3Z_4$)carbonyl" as used herein, means a $NZ_3Z_4$ group, as defined herein, appended to the parent molecular moiety through a carbonyl group, as defined herein. Representative examples of ($NZ_3Z_4$)carbonyl include, but are not limited to, aminocarbonyl, (methylamino)carbonyl, (dimethylamino)carbonyl, and (ethylmethylamino)carbonyl.

The term "($NZ_3Z_4$)sulfonyl" as used herein, means a $NZ_3Z_4$ group, as defined herein, appended to the parent molecular moiety through a sulfonyl group, as defined herein. Representative examples of ($NZ_3Z_4$)sulfonyl include, but are not limited to, aminosulfonyl, (methylamino)sulfonyl, (dimethylamino)sulfonyl, and (ethylmethylamino)sulfonyl.

The term "oxo" as used herein, means a $=O$ moiety.

The term "sulfinyl" as used herein, means a —S(O)— group.

The term "sulfonyl" as used herein, means a —$SO_2$— group.

The term "tautomer" as used herein means a proton shift from one atom of a compound to another atom of the same compound wherein two or more structurally distinct compounds are in equilibrium with each other.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric $(α7)_5$ receptors and α7* receptors, which denote a nAChR containing at least one α7 subunit.

Compounds of the Invention

Compounds of the invention can have the formula (I) as described in the Summary of the Invention.

In compounds of formula (I), $R^1$ is selected from hydrogen and $C_1$-$C_6$ alkyl. Preferably, $R^1$ is hydrogen.

$X_1$ is a bond or is selected from —O—, —O-alkyl, —$NR^2$— and —$NR^2$-alkyl, wherein $R^2$ is selected from hydrogen and $C_1$-$C_6$ alkyl. The oxygen atom of —O-alkyl and the nitrogen atom of —$NR^2$-alkyl each respectively is attached to the parent molecular moiety. A preferred group for $X_1$ is wherein $X_1$ is a bond.

The group represented by A can be a group represented by $Ar^1$, —$Ar^2$—Y—$Ar^3$ or $Ar^4$.

In one embodiment, A represents $Ar^1$. $Ar^1$ is aryl, particularly naphthyl or phenyl. If $X_1$ is a bond and $Ar^1$ is a phenyl ring containing a meta-substituted halogen group, for example chloro, fluoro, or iodo, then the phenyl group can not also be substituted with both a methoxy substitutuent and a —$NH_2$ substituent in addition to the halogen group. Suitable groups for $Ar^1$ are, for example, phenyl, particularly phenyl groups optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, —$NZ_1Z_2$ and ($NZ_3Z_4$)carbonyl; provided that the group is not phenyl, 3,5-dichlorophenyl, or 2-methoxy. More preferred phenyl groups for $Ar^1$ are, for example, 3,4-dichlorophenyl, 4-chlorophenyl, 3-chlorophenyl, 2,3-dichlorophenyl, 2,4-dichlorophenyl, 4-fluorophenyl, 3-fluorophenyl, 4-hydroxyphenyl, 3-hydroxyphenyl, 4-methoxyphenyl, 3-methoxyphenyl, 2-ethoxyphenyl, and 3-trifluoromethoxyphenyl.

Other suitable groups for $Ar^1$ are, for example, naphthyl, particularly naphthyl groups wherein the naphthyl group optionally substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, —$NZ_1Z_2$ and ($NZ_3Z_4$)carbonyl. More preferred naphthyl for $Ar^1$ groups are, for example, 1-naphthyl, 2-naphthyl and 1-hydroxy-2-naphthyl.

When $Ar^1$ is aryl, it is preferred that $X_1$ is a bond.

In another embodiment, A is a group represented by $Ar^2$—Y—$Ar^3$, wherein $Ar^2$ is aryl or heteroaryl; Y is a bond, —O—, —S— and —$NR^3$; and $Ar^3$ is aryl or heteroaryl, and also wherein $Ar^2$, Y and $Ar^3$ are selected independently of each other. Preferably, $Ar^2$ phenyl and a 5 or 6 membered monocyclic heteroaryl ring. $Ar^2$ can be unsubstituted or substituted with 1, 2, 3, 4 or 5 substituents selected from alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, —$NZ_1Z_2$ and ($NZ_3Z_4$)carbonyl, wherein $Z_1$ and $Z_2$ are each independently selected from hydrogen, alkyl, alkylcarbonyl, alkoxycarbonyl, aryl, arylalkyl, formyl and ($NZ_5Z_6$)carbonyl or $Z_1$ and $Z_2$ together with the nitrogen atom to which they are attached form a heterocyclic ring; and $Z_3$ and $Z_4$ are each independently selected from hydrogen, alkyl, aryl and arylalkyl. $Z_5$ and $Z_6$ are each independently selected from hydrogen, alkyl, aryl and arylalkyl. Preferred groups for $Ar^2$ include, but are not limited to, thienyl, furyl, thiazolyl, pyrazolyl, thienyl and phenyl, each of which can be further substituted as described for $Ar^2$. Preferred substituents attached to $Ar^2$ include halo and alkyl.

Preferably, $Ar^3$ is phenyl, a 5 or 6 membered monocyclic heteroaryl ring, or a bicyclic heteroaryl ring. $Ar^3$ can be unsubstituted or substituted with 1,2,3, or 4 substituents selected from alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, —$NZ_1Z_2$ and ($NZ_3Z_4$)carbonyl, wherein $Z_1$, $Z_2$, $Z_3$, and $Z_4$ are as described for $Ar^2$. Preferred groups for $Ar^3$ include, but are not limited to, phenyl, pyridine, thienyl, thiazolyl, trifluoromethylphenyl, and nitrophenyl, each of which can be further substituted as described for $Ar^3$.

When Y is —$NR^3$—, $R^3$ is selected from hydrogen and $C_1$-$C_6$ alkyl. It is preferred that Y is a bond or is —O—. More preferably, Y is a bond. In one embodiment, there is described compounds wherein A is $Ar^2-Y-Ar^3$, $Ar^2$ is thienyl, furyl, thiazolyl or pyrazolyl, Y is a bond and $Ar^3$ is phenyl, pyridinyl or thienyl.

In another embodiment, A is a group represented by $Ar^4$. $Ar^4$ can be heteroaryl or heterocycle, provided that when $X_1$ is a bond $Ar^4$ is not a group that is benzimidazolyl, 2,3-dihydro-1H-indolyl, imidazole[1,2-a]pyridine or 3-indolyl, including further substituted forms of such groups. Preferred $Ar^4$ groups are selected from a 5 or 6 membered heteroaryl ring, a bicyclic heteroaryl ring and a heterocycle. $Ar^4$ can be unsubstituted or substituted with a substituent selected from alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, $-NZ_1Z_2$ and $(NZ_3Z_4)$carbonyl, wherein $Z_1$, $Z_2$, $Z_3$, and $Z_4$ are as previously defined for $Ar^2$. Preferred $Ar^4$ groups include, but are not limited to, benzofuranyl, benzoxadiazolyl, benzoisoxazole, benzoisothiazole, benzooxazole, 1,3-benzothiazolyl, benzodioxolyl, benzothiophenyl, chromenyl, cinnolinyl, furyl, furopyridine, imidazolyl, indolyl, indazolyl, isobenzofuran, isoindolyl, isoquinolinyl, isoxazolyl, isothiazolyl, naphthyridinyl, oxadiazolyl, oxazolyl, oxazolopyridine, pyrazolyl, pyrrolyl, pyridazinyl, pyradinyl, pyrazinyl, pyrimadinyl, quinoxalinyl, quinolinyl, thiazolyl, thienyl, thienopyridine, thiadiazolyl, triazolyl, triazinyl and thienopyridinyl, wherein each group can be further substituted as defined for $Ar^4$. More preferred groups for $Ar^4$ are, for example, 6-(1,3-benzothiazolyl), 5-benzodioxolyl, 2-benzothiophenyl, 3-benzothiophenyl, 5-benzothiophenyl, 3-chromenyl, 5-indolyl, 6-indolyl, furo[2,3-b]pyridinyl, furo[2,3-c]pyridinyl, furo[2,3-b]pyridinyl, furo[3,2-b]pyridinyl, thieno[3,2-c]pyridinyl, thieno[2,3-b]pyridinyl, thieno[2,3-c]pyridinyl, thieno[2,3-b]pyridinyl, thieno[3,2-b]pyridinyl, and thieno[3,2-c]pyridinyl.

Examples of a preferred group include, but are not limited to, compounds of the formula:

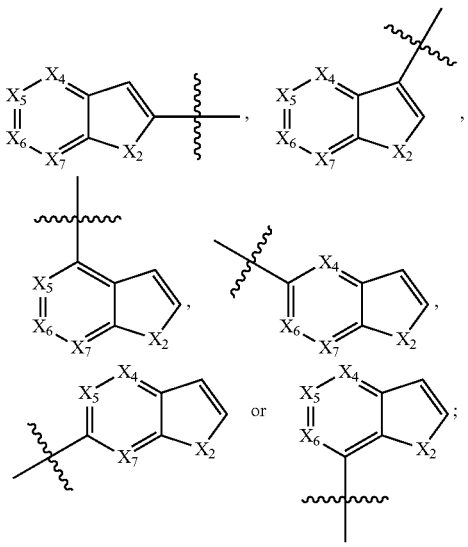

wherein $X_2$ is selected from $-O-$, $-NR_b-$ and $-S-$, one of $X_4$, $X_5$, $X_6$ and $X_7$ may be nitrogen and the others are $CR_a$, each occurance of $R_a$ is independently selected from hydrogen, alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, $-NZ_1Z_2$ and $(NZ_3Z_4)$carbonyl, and $R_b$ is selected from hydrogen and alkyl.

It is preferred that $X_2$ is $-S-$, such that the formulas of above represent the groups wherein $Ar^4$ are:

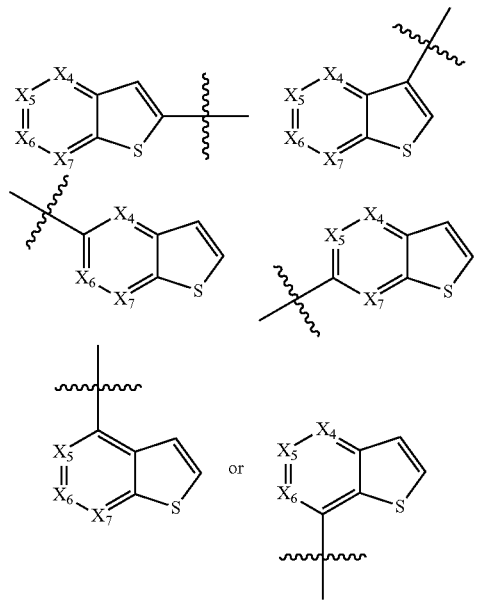

wherein one of $X_4$, $X_5$, $X_6$ and $X_7$ may be nitrogen and the others are $CR_a$, each occurance of $R_a$ is independently selected from hydrogen, alkenyl, alkoxy, alkoxyalkoxy, alkoxyalkyl, alkoxycarbonyl, alkoxycarbonylalkyl, alkyl, alkylcarbonyl, alkylthio, carboxy, carboxyalkyl, cyano, cyanoalkyl, haloalkoxy, haloalkyl, halogen, hydroxy, hydroxyalkyl, nitro, $-NZ_1Z_2$ and $(NZ_3Z_4)$carbonyl. In one particular embodiment, $X_1$ is a bond, and either $X_5$ or $X_6$ is nitrogen.

In one embodiment, $X_1$ is a bond, A is $Ar^4$ and $Ar^4$ is 5-furo[2,3-c]pyridinyl, 5-benzothiophen-yl, 2-(5-phenyl)thiophen-yl, 6-1H-indolyl, 5-(2,2'-bithiophen-yl), 6-thieno[3,2-c]pyridinyl, 3-1H-indazolyl or 5-thieno[2,3-c]pyridinyl.

In another embodiment, $X_1$ is a bond, A is $Ar^4$ and $Ar^4$ is 5-furo[2,3-c]pyridinyl, 6-1H-indolyl, 6-thieno[3,2-c]pyridinyl or 5-thieno[2,3-c]pyridinyl.

All suitable compounds, preferred compounds, and example compounds for $Ar^4$ can be substituted as described for $Ar^4$.

Suitable groups for $X_1$, A, $Ar^1$, $Ar^2$, $Ar^3$, $Ar^4$, Y, $R^1$, $R^2$ and $R^3$ in compounds of formula (I) are independently selected. The described embodiments of the present invention may be combined. Such combination is contemplated and within the scope of the present invention. For example, it is contemplated that preferred groups for any of $X_1$, A, $Ar^1$, $Ar^2$, $Ar^3$, $Ar^4$, Y, $R^1$, $R^2$ and $R^3$ can be combined with groups defined for any other of $X_1$, A, $Ar^1$, $Ar^2$, $Ar^3$, $Ar^4$, Y, $R^1$, $R^2$ and $R^3$ whether or not such group is preferred.

Specific embodiments contemplated as part of the invention include, but are not limited to compounds of formula (I), or salts or prodrugs thereof, for example:

benzo[b]thiophene-2-carboxylic acid (4r)-(1-azatricyclo [3.3.1.1$^{3,7}$]dec-4-yl)-amide;
benzo[b]thiophene-2-carboxylic acid (4s)-(1-azatricyclo [3.3.1.1$^{3,7}$]dec-4-yl)-amide;

benzo[b]thiophene-3-carboxylic acid (4r)-(1-azatricyclo[3.3.1.1$^{3,7}$]dec-4-yl)-amide;
benzo[b]thiophene-3-carboxylic acid (4s)-(1-azatricyclo[3.3.1.1$^{3,7}$]dec-4-yl)-amide;
benzo[b]thiophene-5-carboxylic acid (4r)-(1-azatricyclo[3.3.1.1$^{3,7}$]dec-4-yl)-amide;
benzo[b]thiophene-5-carboxylic acid (4s)-(1-azatricyclo[3.3.1.1$^{3,7}$]dec-4-yl)-amide;
1H-indole-5-carboxylic acid (4r)-(1-azatricyclo[3.3.1.1$^{3,7}$]dec-4-yl)-amide;
1H-indole-5-carboxylic acid (4s)-(1-azatricyclo[3.3.1.1$^{3,7}$]dec-4-yl)-amide;
1H-indole-6-carboxylic acid (4r)-(1-azatricyclo[3.3.1.1$^{3,7}$]dec-4-yl)-amide;
1H-indole-6-carboxylic acid (4s)-(1-azatricyclo[3.3.1.1$^{3,7}$]dec-4-yl)-amide;
thieno[2,3-c]pyridine-5-carboxylic acid (4r)-(1-azatricyclo[3.3.1.1$^{3,7}$]dec-4-yl)-amide;
thieno[2,3-c]pyridine-5-carboxylic acid (4s)-(1-azatricyclo[3.3.1.1$^{3,7}$]dec-4-yl)-amide;
thieno[3,2-c]pyridine-5-carboxylic acid (4r)-(1-azatricyclo[3.3.1.1$^{3,7}$]dec-4-yl)-amide;
thieno[3,2-c]pyridine-5-carboxylic acid (4s)-(1-azatricyclo[3.3.1.1$^{3,7}$]dec-4-yl)-amide;
benzothiazole-6-carboxylic acid (4r)-(1-azatricyclo[3.3.1.1$^{3,7}$]dec-4-yl)-amide;
benzothiazole-6-carboxylic acid (4s)-(1-azatricyclo[3.3.1.1$^{3,7}$]dec-4-yl)-amide;
2-methyl-1H-benzoimidazole-5-carboxylic acid (4r)-(1-azatricyclo[3.3.1.1$^{3,7}$]dec-4-yl)-amide;
2-methyl-1H-benzoimidazole-5-carboxylic acid (4s)-(1-azatricyclo[3.3.1.1$^{3,7}$]dec-4-yl)-amide;
2-aminobenzothiazole-6-carboxylic acid (4r)-(1-azatricyclo[3.3.1.1$^{3,7}$]dec-4-yl)-amide;
5-chlorothiophene-2-carboxylic acid (4r)-(1-azatricyclo[3.3.1.1$^{3,7}$]dec-4-yl)-amide;
5-chlorothiophene-2-carboxylic acid (4s)-(1-azatricyclo[3.3.1.1$^{3,7}$]dec-4-yl)-amide;
4-phenylthiophene-2-carboxylic acid (4r)-(1-azatricyclo[3.3.1.1$^{3,7}$]dec-4-yl)-amide;
4-phenylthiophene-2-carboxylic acid (4s)-(1-azatricyclo[3.3.1.1$^{3,7}$]dec-4-yl)-amide;
5-phenylthiophene-2-carboxylic acid (4r)-(1-azatricyclo[3.3.1.1$^{3,7}$]dec-4-yl)-amide;
5-phenylthiophene-2-carboxylic acid (4s)-(1-azatricyclo[3.3.1.1$^{3,7}$]dec-4-yl)-amide;
5-(pyridin-2-yl)-thiophene-2-carboxylic acid (4r)-(1-azatricyclo[3.3.1.1$^{3,7}$]dec-4-yl)-amide;
5-(pyridin-2-yl)-thiophene-2-carboxylic acid (4s)-(1-azatricyclo[3.3.1.1$^{3,7}$]dec-4-yl)-amide;
2,2'-bithiophene-5-carboxylic acid (4r)-(1-azatricyclo[3.3.1.1$^{3,7}$]dec-4-yl)-amide;
2,2'-bithiophene-5-carboxylic acid (4s)-(1-azatricyclo[3.3.1.1$^{3,7}$]dec-4-yl)-amide;
5-(3-trifluoromethylphenyl)-furan-2-carboxylic acid (4r)-(1-azatricyclo[3.3.1.1$^{3,7}$]dec-4-yl)-amide;
5-(3-trifluoromethylphenyl)-furan-2-carboxylic acid (4s)-(1-azatricyclo[3.3.1.1$^{3,7}$]dec-4-yl)-amide;
5-(2-nitrophenyl)-furan-2-carboxylic acid (4r)-(1-azatricyclo[3.3.1.1$^{3,7}$]dec-4-yl)-amide;
5-(2-nitrophenyl)-furan-2-carboxylic acid (4s)-(1-azatricyclo[3.3.1.1$^{3,7}$]dec-4-yl)-amide;
2-(pyridin-4-yl)-thiazole-2-carboxylic acid (4r)-(1-azatricyclo[3.3.1.1$^{3,7}$]dec-4-yl)-amide;
2-(pyridin-4-yl)-thiazole-2-carboxylic acid (4s)-(1-azatricyclo[3.3.1.1$^{3,7}$]dec-4-yl)-amide;
2-(thiophen-2-yl)-thiazole-4-carboxylic acid (4r)-(1-azatricyclo[3.3.1.1$^{3,7}$]dec-4-yl)-amide;
5-(thiophen-2-yl)-1H-pyrazole-3-carboxylic acid (4r)-(1-azatricyclo[3.3.1.1$^{3,7}$]dec-4-yl)-amide;
N-[(4r)-1-azatricyclo[3.3.1.1$^{3,7}$]dec-4-yl]-4-(thiophen-2-yl)-benzamide;
N-[(4s)-1-azatricyclo[3.3.1.1$^{3,7}$]dec-4-yl]-4-(thiophen-2-yl)-benzamide;
N-[(4r)-1-azatricyclo[3.3.1.1$^{3,7}$]dec-4-yl]-3,4-dichlorobenzamide;
N-[(4s)-1-azatricyclo[3.3.1.1$^{3,7}$]dec-4-yl]-3,4-dichlorobenzamide;
N-[(4r)-1-azatricyclo[3.3.1.1$^{3,7}$]dec-4-yl]-4-chlorobenzamide;
N-[(4s)-1-azatricyclo[3.3.1.1$^{3,7}$]dec-4-yl]-4-chlorobenzamide;
N-[(4s)-1-azatricyclo[3.3.1.1$^{3,7}$]dec-4-yl]-3-chlorobenzamide;
N-[(4s)-1-azatricyclo[3.3.1.1$^{3,7}$]dec-4-yl]-2,3-dichlorobenzamide;
N-[(4s)-1-azatricyclo[3.3.1.1$^{3,7}$]dec-4-yl]-2,4-dichlorobenzamide;
N-[(4s)-1-azatricyclo[3.3.1.1$^{3,7}$]dec-4-yl]-4-fluorobenzamide;
N-[(4s)-1-azatricyclo[3.3.1.1$^{3,7}$]dec-4-yl]-3-fluorobenzamide;
N-[(4s)-1-azatricyclo[3.3.1.1$^{3,7}$]dec-4-yl]-4-hydroxybenzamide;
N-[(4s)-1-azatricyclo[3.3.1.1$^{3,7}$]dec-4-yl]-3-hydroxybenzamide;
N-[(4s)-1-azatricyclo[3.3.1.1$^{3,7}$]dec-4-yl]-4-methoxybenzamide;
N-[(4s)-1-azatricyclo[3.3.1.1$^{3,7}$]dec-4-yl]-3-methoxybenzamide;
N-[(4s)-1-azatricyclo[3.3.1.1$^{3,7}$]dec-4-yl]-2-ethoxybenzamide;
N-[(4s)-1-azatricyclo[3.3.1.1$^{3,7}$]dec-4-yl]-3-trifluoromethoxybenzamide;
N-[(4s)-1-azatricyclo[3.3.1.1$^{3,7}$]dec-4-yl]-4-phenoxybenzamide;
N-[(4s)-1-azatricyclo[3.3.1.1$^{3,7}$]dec-4-yl]-4-methylsulfanyl-benzamide;
thiophene-2-carboxylic acid (4s)-(1-azatricyclo[3.3.1.1$^{3,7}$]dec-4-yl)-amide;
5-methylthiophene-2-carboxylic acid (4s)-(1-azatricyclo[3.3.1.1$^{3,7}$]dec-4-yl)-amide;
3-methylthiophene-2-carboxylic acid (4s)-(1-azatricyclo[3.3.1.1$^{3,7}$]dec-4-yl)-amide;
naphthalene-2-carboxylic acid (4s)-(1-azatricyclo[3.3.1.1$^{3,7}$]dec-4-yl)-amide;
1-hydroxynaphthalene-2-carboxylic acid (4s)-(1-azatricyclo[3.3.1.1$^{3,7}$]dec-4-yl)-amide;
naphthalene-1-carboxylic acid (4s)-(1-azatricyclo[3.3.1.1$^{3,7}$]dec-4-yl)-amide;
6-chloro-2H-chromene-3-carboxylic acid (4s)-(1-azatricyclo[3.3.1.1$^{3,7}$]dec-4-yl)-amide;
benzo[1,3]dioxole-5-carboxylic acid (4s)-(1-azatricyclo[3.3.1.1$^{3,7}$]dec-4-yl)-amide;
2,3-dihydrobenzo[1,4]dioxine-6-carboxylic acid (4r)-(1-azatricyclo[3.3.1.1$^{3,7}$]dec-4-yl)-amide;
2,3-dihydrobenzo[1,4]dioxine-6-carboxylic acid (4s)-(1-azatricyclo[3.3.1.1$^{3,7}$]dec-4-yl)-amide;
furo[2,3-c]pyridine-5-carboxylic acid (1-aza-tricyclo[3.3.1.1$^{3,7}$]dec-4-yl)-amide;
3-methyl-benzofuran-2-carboxylic acid (1-aza-tricyclo[3.3.1.1$^{3,7}$]dec-4-yl)-amide;

furo[2,3-c]pyridine-5-carboxylic acid (1-aza-tricyclo[3.3.1.1^{3,7}]dec-4-yl)-amide;
2-naphthoic acid (4r)-(1-azatricyclo[3.3.1.1^{3,7}]dec-4-yl)-amide;
benzofuran-2-carboxylic acid (4r)-(1-azatricyclo[3.3.1.1^{3,7}]dec-4-yl)-amide;
benzo[d][1,2,3]thiadiazole-5-carboxylic acid (4r)-(1-azatricyclo[3.3.1.1^{3,7}]dec-4-yl)-amide;
isoquinoline-3-carboxylic acid (4r)-(1-azatricyclo[3.3.1.1^{3,7}]dec-4-yl)-amide;
benzo[c][1,2,5]thiadiazole-5-carboxylic acid (4r)-(1-azatricyclo[3.3.1.1^{3,7}]dec-4-yl)-amide;
5-(2-methylthiazol-4-yl)thiophene-2-carboxylic acid (4r)-(1-azatricyclo[3.3.1.1^{3,7}]dec-4-yl)-amide;
3-thiophen-2-yl)benzoic acid (4r)-(1-azatricyclo[3.3.1.1^{3,7}]dec-4-yl)-amide;
thieno[3,2-b]thiophene-2-carboxylic acid (4r)-(1-azatricyclo[3.3.1.1^{3,7}]dec-4-yl)-amide;
thieno[2,3-b]thiophene-2-carboxylic acid (4r)-(1-azatricyclo[3.3.1.1^{3,7}]dec-4-yl)-amide;
5-chlorobenzofuran-2-carboxylic acid (4r)-(1-azatricyclo[3.3.1.1^{3,7}]dec-4-yl)-amide;
1H-indazole-3-carboxylic acid (4r)-(1-azatricyclo[3.3.1.1^{3,7}]dec-4-yl)-amide; and
1H-indazole-4-carboxylic acid (4r)-(1-azatricyclo[3.3.1.1^{3,7}]dec-4-yl)-amide.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

More particularly, the compounds of the present invention exist in the forms represented by formula (Ia) and (Ib)

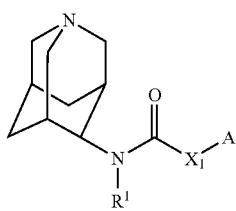

(Ia)

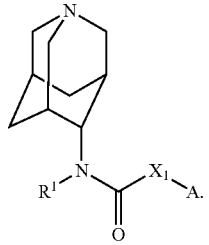

(Ib)

The isomers (Ia) and (Ib) may be either synthesized separately by using the individual steroisomers according to the Schemes and/or the experimentals described herein. Alternatively, the individual isomers may be separated by chromatographic methods from the mixture of both isomers when mixtures of stereoisomers are used in the synthesis. It is contemplated that a mixture of both isomers may be used to modulate the effects of nAChRs. Furthermore, it is contemplated that the individual isomers of formula (Ia) and (Ib) may be used alone to modulate the effects of nAChRs. Therefore, it is contemplated that either a mixture of the compounds of formula (Ia) and (Ib) or the individual isomers alone represented by the compounds of formula (Ia) or (Ib) would be effective in modulating the effects of nAChRs, and more particularly α7 nAChRs and is thus within the scope of the present invention.

More specifically, preferred compounds contemplated as part of the invention include
furo[2,3-c]pyridine-5-carboxylic acid (1-aza-tricyclo[3.3.1.1^{3,7}]dec-4-yl)-amide;
furo[2,3-c]pyridine-5-carboxylic acid (1-aza-tricyclo[3.3.1.1^{3,7}]dec-4-yl)-amide;
benzo[b]thiophene-5-carboxylic acid (4s)-(1-azatricyclo[3.3.1.1^{3,7}]dec-4-yl)-amide;
benzo[b]thiophene-5-carboxylic acid (4r)-(1-azatricyclo[3.3.1.1^{3,7}]dec-4-yl)-amide;
benzo[b]thiophene-2-carboxylic acid (4s)-(1-azatricyclo[3.3.1.1^{3,7}]dec-4-yl)-amide;
5-phenylthiophene-2-carboxylic acid (4r)-(1-azatricyclo[3.3.1.1^{3,7}]dec-4-yl)-amide;
1H-indole-6-carboxylic acid (4s)-(1-azatricyclo[3.3.1.1^{3,7}]dec-4-yl)-amide;
2,2'-bithiophene-5-carboxylic acid (4s)-(1-azatricyclo[3.3.1.1^{3,7}]dec-4-yl)-amide;
2,2'-bithiophene-5-carboxylic acid (4r)-(1-azatricyclo[3.3.1.1^{3,7}]dec-4-yl)-amide;
thieno[3,2-c]pyridine-5-carboxylic acid (4s)-(1-azatricyclo[3.3.1.1^{3,7}]dec-4-yl)-amide;
thieno[2,3-c]pyridine-5-carboxylic acid (4s)-(1-azatricyclo[3.3.1.1^{3,7}]dec-4-yl)-amide;
thieno[3,2-c]pyridine-5-carboxylic acid (4r)-(1-azatricyclo[3.3.1.1^{3,7}]dec-4-yl)-amide;
thieno[2,3-c]pyridine-5-carboxylic acid (4r)-(1-azatricyclo[3.3.1.1^{3,7}]dec-4-yl)-amide; and
1H-indazole-3-carboxylic acid (4r)-(1-azatricyclo[3.3.1.1^{3,7}]dec-4-yl)-amide.

In addition, other preferred compounds contemplated as part of the invention include
furo[2,3-c]pyridine-5-carboxylic acid (1-aza-tricyclo[3.3.1.1^{3,7}]dec-4-yl)-amide;
1H-Indole-6-carboxylic acid (4s)-(1-azatricyclo[3.3.1.1^{3,7}]dec-4-yl)-amide;
thieno[3,2-c]pyridine-5-carboxylic acid (4s)-(1-azatricyclo[3.3.1.1^{3,7}]dec-4-yl)-amide; and thieno[2,3-c]pyridine-5-carboxylic acid (4s)-(1-azatricyclo [3.3.1.1$^{3,7}$]dec-4-yl)-amide.

Methods of the Invention

Compounds and compositions of the invention are useful for modulating the effects of nAChRs, and more particularly α7 nAChRs. In particular, the compounds and compositions of the invention can be used for treating or preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

In addition, the invention relates to a method for treating or preventing a condition or disorder modulated by an α7 nicotinic acetylcholine receptor comprising the step of administering a compound of the formula (II)

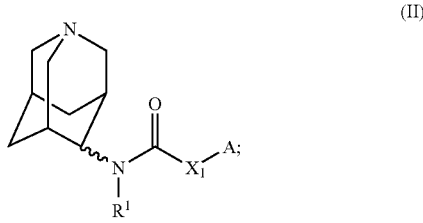

(II)

or a pharmaceutically suitable salt or prodrug thereof, wherein $X_1$ is a bond or is selected from —O—, —O-alkyl, —NR$^2$— and —NR$^2$-alkyl; A is selected from Ar$^1$, —Ar$^2$—Y—Ar$^3$ and Ar$^4$; Ar$^1$ is aryl; Ar$^2$ is selected from aryl and heteroaryl; Ar$^3$ is selected from aryl and heteroaryl; Ar$^4$ is selected from heteroaryl and heterocycle; Y is a bond or is selected from —O—, —S— and —NR$^3$—; and R$^1$, R$^2$ and R$^3$ are individually selected from hydrogen and C$_1$-C$_6$ alkyl. Preferred compounds are compounds of formula (I), which are within the scope of formula (II). Preferred embodiments for compounds of formula (II) are as described for compounds of formula (I).

The invention also contemplates the method for treating or preventing a condition or disorder modulated by an α7 nicotinic acetylcholine receptor comprising the step of administering a compound of the formula (II), wherein the condition or disorder is selected from a memory disorder, cognitive disorder, neurodegeneration, and neurodevelopmental disorder.

The invention also contemplates a method for treating or preventing a condition or disorder modulated by an α7 nicotinic acetylcholine receptor comprising the step of administering a compound of the formula (II), wherein the condition or disorder is selected from attention deficit disorder, attention deficit hyperactivity disorder (ADHD), Alzheimer's disease (AD), mild cognitive impairment, schizophrenia, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain and inflammatory pain.

The invention also contemplates a method for treating or preventing a condition or disorder modulated by an α7 nicotinic acetylcholine receptor comprising the step of administering a compound of the formula (II), wherein the condition or disorder is schizophrenia.

The invention also contemplates a method for treating or preventing a condition or disorder modulated by an α7 nicotinic acetylcholine receptor comprising the step of administering a compound of the formula (II) in combination with an atypical antipsychotic.

The invention also contemplates a method for treating or preventing a condition or disorder modulated by an α7 nicotinic acetylcholine receptor comprising the step of administering a compound of the formula (II), wherein the condition or disorder is infertility, lack of circulation, need for new blood vessel growth associated with wound healing, more particularly circulation around a vascular occlusion, need for new blood vessel growth associated with vascularization of skin grafts, ischemia, inflammation, wound healing, and other complications associated with diabetes.

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions.

Specific examples of compounds that can be useful for the treatment or prevention of α7 nAChR-mediated diseases or conditions include, but are not limited to, compounds described in the Compounds of the Invention and also in the Examples, and also compounds such as N-(1-aza-tricyclo[3.3.1.1$^{3,7}$]dec-4-yl)-benzamide;

N-(1-aza-tricyclo[3.3.1.1$^{3,7}$]dec-4-yl)-3,5-dichloro-benzamide;

N-(1-aza-tricyclo[3.3.1.1$^{3,7}$]dec-4-yl)-2-methoxy-benzamide;

1-H-indole-3-carboxylic acid (1-aza-tricyclo[3.3.1.1$^{3,7}$]dec-4-yl)-amide;

(4α,β)-4-amino-N-[1-azaadamantan-4-yl]-5-chloro-2-methoxy benzamide;

6-chloro-imidazo[1,2-a]pyridine-8-carboxylic acid (1-aza-tricyclo[3.3.1.1$^{3,7}$]dec-4-yl)amide; and 3-ethyl-indolizine-1-carboxylic acid (1-aza-tricyclo [3.3.1.1$^{3,7}$]dec-4-yl)-amide.

Methods for preparing compounds useful in the method of the invention also can be found in Iriepa, I, et al. *J. Molec. Struct.* 1999, 509, 105; Flynn, D. L., et al. *BMCL* 1992, 2, 1613; U.S. Pat. No. 4,816,453; WO 94/00454; U.S. Pat. No. 5,280,028; U.S. Pat. No. 5,399,562; WO 92/15593; U.S. Pat. No. 5,260,303; U.S. Pat. No. 5,591,749; U.S. Pat. No. 5,434,151; and U.S. Pat. No. 5,604,239.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Alpha-7 nAChRs also have been implicated in aspects of neurodevelopment, for example neurogenesis of the brain. (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 nAChRs can be useful in preventing or treating conditions or disorders associated with impaired neurodevelopment, for example schizophrenia. (Sawa A., Mol. Med. 9:3-9, 2003).

Schizophrenia is a complex disease that is characterized by abnormalities in perception, cognition, and emotions. Significant evidence implicates the involvement of α7 nAChRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al, J. Clin. Invest. 110: 527-536, 2002). For example, improved conditions related to inflammation, ischemia, cardiac ischemia, and wound healing, for example in diabetic persons, have been associated with α7 nAChR activity (Jacobi, J., et al., Am. J. Pathol. 161:97-104, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting memory, cognition, neurodegeneration, neurodevelopment, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

As used in the descriptions of the schemes and the examples, certain abbreviations are intended to have the following meanings: Ac for acetyl; Bu for n-butyl; Bn for benzyl; cat. for cataylst; dba for dibenzylidene acetone; DMF for dimethyl formamide; EtOH for ethanol; Et$_3$N for triethylamine; EtOAc for ethyl acetate; HPLC for high pressure liquid chromatography; $^i$Pr for isopropyl; $^i$PrOAc for isopropyl acetate; LAH for lithium aluminum hydride; Me for methyl; MeOH for methanol; NBS for N-bromosuccinimide; NMP for N-methylpyrrolidine; OAc for acetoxy; ONF for nonaflate or —OSO$_2$CF$_2$CF$_2$CF$_3$; Pd/C for palladium on carbon; Ph for phenyl; Rh/C for rhodium on carbon; $^t$Bu for tert-butyl; $^t$BuO for tert-butoxide; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the BOC protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

Scheme 1

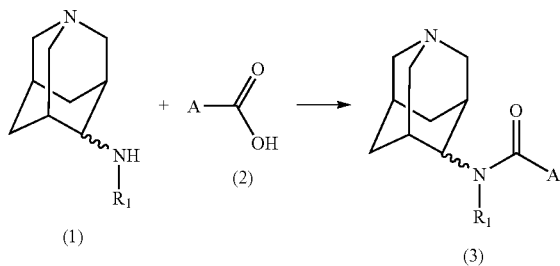

As shown in Scheme 1, compounds of formula (1) which are prepared as outlined in Becker, D. P.; Flynn, D. L., Synthesis, 1992, 1080, when treated with a carboxylic acid of formula (2) utilizing conditions known to those skilled in the art which couple carboxylic acids to amines to generate amides, will provide compounds of formula (3) which are representative of compounds of the present invention. Examples of conditions known to generate amides from a mixture of a carboxylic acid and an amine include but are not limited to adding a coupling reagent such as but not limited to 1-(3-dimethylaminopropyl)-3-ethylcarbodiimide hydrochloride (EDCI), 1,3-dicyclohexylcarbodiimide (DCC), Bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to 1-Hydroxy-7-azabenzotriazole (HOAT) and 1-hydroxybenzotriazole hydrate (HOBT). The coupling reaction may be carried out in solvents such as but not limited to THF, DMA dichloromethane, ethyl acetate and the like.

Scheme 2

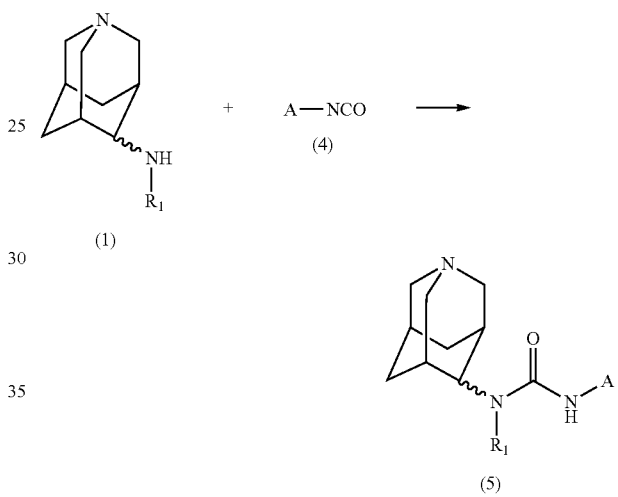

As shown in Scheme 2, the treatment of amines of formula (1) with an isocyanate of formula (4) will provide compounds of formula (5) which are representative of the compounds of the present invention wherein X$_1$ is —NR$^2$— and R$^2$ is hydrogen. The reaction may be carried out with or without a solvent for example THF and DME.

Scheme 3

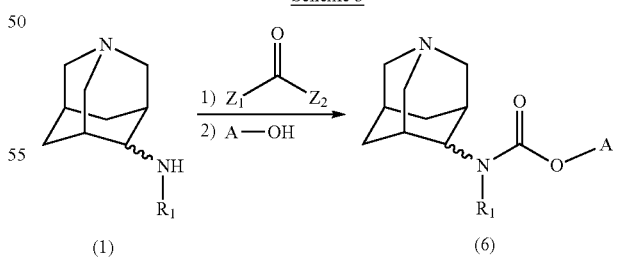

As shown in Scheme 3, the treatment of amines of formula (1) with reagents of general formula (Z$_1$Z$_2$)C=O, wherein Z$_1$ and Z$_2$ are selected from chloro, imidazole, succinimide and the like, followed by treatment with compounds of general formula A-OH will provide compounds of formula (6) which are representative of compounds of the present invention wherein X$_1$ is —O—. Compounds of general formula (Z$_1$Z$_2$)

C=O, may also be replaced with such reagents as triphosgene and others known by one skilled in the art.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalene-sulfonate, oxalate, pamoate, pectinate, persulfate, 3-phenyl-propionate, picrate, pivalate, propionate, succinate, tartrate, thiocyanate, phosphate, glutamate, bicarbonate, p-toluene-sulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

The compounds of the invention and processes for making compounds for the method of the invention will be better understood by reference to the following Examples, which are intended as an illustration of and not a limitation upon the scope of the invention.

EXAMPLES

Procedure for Amide Formation (Method A)

A suspension of (4s)- or (4r)-1-azatricyclo[3.3.1.1$^{3,7}$]dec-4-ylamine hydrochloride (60 mg, 0.32 mmol; prepared according to Becker, D. P.; Flynn, D. L. *Synthesis* 1992, 1080) and the carboxylic acid (1 equiv) in anhydrous THF (2 mL) was treated with N,N-diisopropylethylamine (iPr$_2$NEt; 120 µL, 0.93 mmol, 2.9 equiv; Acros) and O-(7-azabenzotriazol-1-yl)-N,N,N',N'-tetramethyluronium hexafluorophosphate (HATU; 130 mg, 0.34 mmol, 1.1 equiv; Aldrich). The mixture was stirred overnight, diluted with methanol (5 mL) and filtered. The filtrate was concentrated in vacuo and the resulting material was purified by preparative HPLC [Waters XTerra RP$_{18}$ 30×100 mm column, flow rate 40 mL/min, 5-95% gradient of acetonitrile in buffer (0.1M aq. ammonium bicarbonate, adjusted to pH 10 with sodium hydroxide)] to afford the desired amide product as its free base. Alternatively, the compound was purified on a Waters Symmetry C$_{8\text{-}30\times100}$ mm column (flow rate 40 mL/min, 5-95% gradient of acetonitrile in 0.1% aqueous trifluoroacetic acid) to afford the amide product as its trifluoroacetate salt after evaporation of solvent.

Procedure for Amide Formation (Method B)

A Smith Process vessel (0.5-2 mL) containing a stir bar was charged with polymer-bound N-benzyl-N'-cyclohexylcarbodiimide (PS-DCC; 3 equiv; Argonaut) followed by the carboxylic acid (1.1 equiv), N,N-diisopropylethylamine (iPr$_2$NEt; 3 equiv; Aldrich), and solutions of 1-hydroxybenzotriazole (HOBt; 1 equiv; Aldrich) and (4s)-1-azatricyclo[3.3.1.1$^{3,7}$]dec-4-ylamine (17.5 mg, 1 equiv; prepared according to Becker, D. P.; Flynn, D. L. *Synthesis* 1992, 1080) in N,N-dimethylacetamide (DMA). The reaction vessel was then sealed and heated at 100° C. in a microwave for 420-600 s. After cooling, the reaction vessel was uncapped and the mixture filtered through a column packed with Si-Carbonate (polymer-bound carbonate, Silicycle; 2 g), eluting with methanol. The filtrate was collected, dried, and purified by reverse-phase HPLC to afford the desired product.

Procedure for Salt Formation (Method C)

A rapidly stirring solution of the amide free base (from the previous step) in ethyl acetate or ethyl acetate-ethanol (1:1) was treated with either HCl-dioxane (1-2 equiv, 4 M; Aldrich) or p-toluenesulfonic acid monohydrate (1 equiv; Aldrich) at room temperature. After stirring for 2 hours, the precipitate was collected by filtration and dried to afford the title compound.

Example 1

Benzo[b]thiophene-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and thianaphthene-2-carboxylic acid (Aldrich) according to methods A and C; yield 55 mg, 0.16 mmol (50%): $^1$H NMR (300 MHz, methanol-d4) δ 2.08-2.29 (m, 5H), 2.49 (s, 2 H), 3.50 (d, J=13 Hz, 2H), 3.56 (s, 2H), 3.85 (d, J=13 Hz, 2H), 4.28 (t, J=3 Hz, 1H), 7.38-7.50 (m, 2H), 7.87-7.96 (m, 2H), 8.14 (d, J=1 Hz, 1H); MS (DCI/NH$_3$) m/z 313 (M+H)$^+$; Anal. C$_{18}$H$_{20}$N$_2$OS.HCl.0.3H$_2$O: C, H, N.

Example 2

Benzo[b]thiophene-2-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and thianaphthene-2-carboxylic acid (Aldrich) according to methods A and C; yield 57 mg, 0.16 mmol (50%): $^1$H NMR (300 MHz, methanol-d4) δ 1.98 (d, J=13 Hz, 2H), 2.20 (s, 1 H), 2.36 (d, J=14 Hz, 2H), 2.49 (s, 2H), 3.57 (s, 2H), 3.67 (d, J=2 Hz, 4H), 4.42 (s, 1 H), 7.39-7.50 (m, 2H), 7.88-7.96 (m, 2H), 8.12 (s, 1H); MS (DCI/NH$_3$) m/z 313 (M+H)$^+$; Anal. C$_{18}$H$_{20}$N$_2$OS.HCl.0.12H$_2$O: C, H, N.

Example 3

Benzo[b]thiophene-3-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 1-benzothiophene-3-carboxylic acid (Maybridge) according to methods A and C; yield 60 mg, 0.17 mmol (56%): $^1$H NMR (300 MHz, methanol-d4) δ 2.10-2.30 (m, 5H), 2.48 (s, 2H), 3.50 (d, J=13 Hz, 2H), 3.56 (s, 2H), 3.83 (d, J=13 Hz, 2H), 4.33 (s, 1H), 7.36-7.49 (m, 2H), 7.91-7.96 (m, 1H), 8.28-8.34 (m, 2H); MS (DCI/NH$_3$) m/z 313 (M+H)$^+$; Anal. C$_{18}$H$_{20}$N$_2$OS.HCl.0.17H$_2$O: C, H, N.

Example 4

Benzo[b]thiophene-3-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 1-benzothiophene-3-carboxylic acid (Maybridge) according to methods A and C; yield 58 mg, 0.17 mmol (56%): $^1$H NMR (300 MHz, methanol-d4) δ 1.98 (d, J=13 Hz, 2H), 2.20 (s, 1H), 2.36 (d, J=14 Hz, 2H), 2.48 (s, 2H), 3.57 (s, 2H), 3.69 (d, J=2 Hz, 4H), 4.47 (s, 1H), 7.38-7.48 (m, 2H), 7.92-7.96 (m, 1H), 8.27 (s, 1H), 8.27-8.32 (m, 1H); MS (DCI/NH$_3$) m/z 313 (M+H)$^+$; Anal. C$_{18}$H$_{20}$N$_2$OS.HCl.0.13H$_2$O: C, H, N.

Example 5

Benzo[b]thiophene-5-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 5-benzothiophene-3-carboxylic acid (Maybridge) according to methods A and C; yield 76 mg, 0.21 mmol (66%): $^1$H NMR (300 MHz, methanol-d4) δ 2.09-2.29 (m, 5H), 2.49 (s, 2H), 3.45-3.59 (m, 4H), 3.85 (d, J=13 Hz, 2H), 4.31 (s, 1H), 7.49 (d, J=5 Hz, 1H), 7.70 (d, J=5 Hz, 1H), 7.84 (dd, J=8, 2 Hz, 1H), 8.01 (d, J=8 Hz, 1H), 8.40 (d, J=2 Hz, 1H); MS (DCI/NH$_3$) m/z 313 (M+H)$^+$; Anal. C$_{18}$H$_{20}$N$_2$OS.HCl.0.75H$_2$O: C, H, N.

Example 6

Benzo[b]thiophene-5-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 5-benzothiophene-3-carboxylic acid (Maybridge) according to methods A and C; yield 64 mg, 0.18 mmol (56%): $^1$H NMR (300 MHz, methanol-d4) δ 1.98 (d, J=14 Hz, 2H), 2.21 (s, 1H), 2.37 (d, J=14 Hz, 2H), 2.49 (s, 2H), 3.57 (s, 2H), 3.69 (d, J=1 Hz, 4H), 4.44 (s, 1H), 7.50 (d, J=5 Hz, 1H), 7.70 (d, J=6 Hz, 1H), 7.81 (dd, J=8, 2 Hz, 1H), 8.02 (d, J=8 Hz, 1H), 8.37 (d, J=2 Hz, 1H); MS (DCI/NH$_3$) m/z 313 (M+H)$^+$; Anal. C$_{18}$H$_{20}$N$_2$OS.HCl.0.22H$_2$O: C, H, N.

Example 7

1H-Indole-5-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and indole-5-carboxylic acid (Aldrich) according to methods A and C; yield 77 mg, 0.23 mmol (65%): $^1$H NMR (300 MHz, methanol-d4) δ 2.00-2.31 (m, 5H), 2.48 (s, 2H), 3.49 (d, J=12 Hz, 2H), 3.56 (s, 2H), 3.85 (d, J=13 Hz, 2H), 4.31 (d, 1H), 6.57 (d, J=3 Hz, 1H), 7.33 (d, J=3 Hz, 1H), 7.44 (d, J=9 Hz, 1H), 7.66 (dd, J=9, 2 Hz, 1H), 8.18 (d, J=2 Hz, 1H); MS (DCI/NH$_3$) m/z 296 (M+H)$^+$; Anal. C$_{18}$H$_{21}$N$_3$O.HCl.0.1H$_2$O: C, H, N.

Example 8

1H-Indole-5-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and indole-5-carboxylic acid (Aldrich) according to methods A and C; yield 27 mg, 0.08 mmol (37%): $^1$H NMR (300 MHz, methanol-d4) δ 1.97 (d, J=13 Hz, 2H), 2.21 (s, 1H), 2.37 (d, J=14 Hz, 2H), 2.49 (s, 2H), 3.58 (s, 2H), 3.69 (s, 4H), 4.42 (s, 1H), 6.57 (dd, J=3, 1 Hz, 1H), 7.34 (d, J=3 Hz, 1H), 7.45 (d, J=8 Hz, 1H), 7.64 (dd, J=9, 2 Hz, 1H), 8.10-8.17 (m, 2H); MS (DCI/NH$_3$) m/z 296 (M+H)$^+$; Anal. C$_{18}$H$_{21}$N$_3$O.HCl.0.5H$_2$O: C, H, N.

Example 9

1H-Indole-6-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and indole-6-carboxylic acid (Lancaster) according to methods A and C; yield 59 mg, 0.17 mmol (48%): $^1$H NMR (300 MHz, methanol-d4) δ 2.12-2.30 (m, 6H), 2.49 (s, 2H), 3.49 (d, J=12 Hz, 2H), 3.56 (s, 2H), 3.85 (d, J=13 Hz, 2H), 4.29 (s, 1H), 7.41 (d, J=3 Hz, 1H), 7.55 (dd, J=8, 2 Hz, 1H), 7.62 (d, J=12 Hz, 1H), 7.94-8.04 (m, 1H), 8.22 (d, J=5 Hz, 1H); MS (DCI/NH$_3$) m/z 296 (M+H)$^+$; Anal. C$_{18}$H$_{21}$N$_3$O.HCl.0.75H$_2$O: C, H, N.

Example 10

1H-Indole-6-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and indole-6-carboxylic acid (Lancaster) according to methods A and C; yield 91 mg, 0.25 mmol (69%): $^1$H NMR (300 MHz, methanol-d4) δ 1.98 (d, J=13 Hz, 2H), 2.21 (s, 1H), 2.36 (d, J=13 Hz, 2H), 2.49 (s, 2H), 3.58 (s, 2H), 3.69 (s, 4H), 4.42 (s, 1H), 6.52 (dd, J=3, 1 Hz, 1H), 7.41 (d, J=3 Hz, 1H), 7.52 (dd, J=8, 2 Hz, 1H), 7.63 (dd, J=8, 1 Hz, 1H), 7.93-7.99 (m, 1H); MS (DCI/NH$_3$) m/z 296 (M+H)$^+$; Anal. C$_{18}$H$_{21}$N$_3$O.HCl.1.1H$_2$O.0.2C$_4$H$_8$O$_2$: C, H, N.

Example 11

Thieno[2,3-c]pyridine-5-carboxylic acid (4r)-(1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and thieno[2,3-c]pyridine-5-carboxylic acid (*Tetrahedron Lett.* 1999, 40, 7935) according to methods A and C; yield 73 mg, 0.18 mmol (51%): $^1$H NMR (300 MHz, methanol-d4) δ 2.12-2.33 (m, 5H), 2.55 (s, 2H), 3.53 (d, J=12 Hz, 2H), 3.59 (s, 2H), 3.99 (d, J=13 Hz, 2H), 4.40 (s, 1H), 7.94 (d, J=5 Hz, 1H), 8.65 (d, J=5 Hz, 1H), 9.15 (s, 1H), 9.59 (s, 1H); MS (DCI/NH$_3$) m/z 296 (M+H)$^+$; Anal. C$_{17}$H$_{19}$N$_3$OS.2HCl.0.6H$_2$O: C, H, N.

Example 12

Thieno[2,3-c]pyridine-5-carboxylic acid (4s)-(1-azatricyclo[3.3.1.1$^{3,7}$]dec-4-yl)-amide dihydrochloride Prepared from (4s)-1-azatricyclo[3.3.1.1$^{3,7}$]dec-4-ylamine hydrochloride and thieno[2,3-c]pyridine-5-carboxylic acid (*Tetrahedron Lett.* 1999, 40, 7935) according to methods A and C; yield 82 mg, 0.21 mmol (59%): $^1$H NMR (300 MHz, methanol-d4) δ 2.03 (d, J=14 Hz, 2H), 2.25 (s, 1H), 2.39 (d, J=14 Hz, 2H), 2.55 (s, 2H), 3.61 (s, 2H), 3.72 (s, 4H), 4.54 (s, 1H), 7.91 (d, J=5 Hz, 1H), 8.62 (d, J=5 Hz, 1H), 9.01 (s, 1H), 9.57 (s, 1H); MS (DCI/NH$_3$) m/z 314 (M+H)$^+$; Anal. C$_{17}$H$_{19}$N$_3$OS.2HCl.1.0H$_2$O: C, H, N.

Example 13

Thieno[3,2-c]pyridine-5-carboxylic acid (4r)-(1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and thieno[3,2-c]pyridine-6-carboxylic acid (*Tetrahedron Lett.* 1999, 40, 7935) according to methods A and C; yield 69 mg, 0.18 mmol (55%): $^1$H NMR (300 MHz, methanol-d4) δ 2.06-2.33 (m, 5H), 2.55 (s, 2H), 3.53 (d, J=13 Hz, 2H), 3.59 (s, 2H), 3.98 (d, J=13 Hz, 2H), 4.40 (s, 1H), 7.98 (d, J=5 Hz, 1H), 8.34 (d, J=5 Hz, 1H), 9.37 (s, 1H), 9.44 (s, 1H); MS (DCI/NH$_3$) m/z 314 (M+H)$^+$; Anal. C$_{17}$H$_{19}$N$_3$OS.2HCl.1.5H$_2$O: C, H, N.

Example 14

Thieno[3,2-c]pyridine-5-carboxylic acid (4s)-(1-azatricyclo[3.3.1.1$^{3,7}$]dec-4-yl)-amide dihydrochloride (78299-38, A-873053.3)

Prepared from (4s)-1-azatricyclo[3.3.1.1$^{3,7}$]dec-4-ylamine hydrochloride and thieno[3,2-c]pyridine-6-carboxylic acid (*Tetrahedron Lett.* 1999, 40, 7935) according to methods A and C; yield 111 mg, 0.21 mmol (73%): $^1$H NMR (300 MHz, methanol-d4) δ 2.03 (d, J=13 Hz, 2H), 2.25 (s, 1H), 2.37 (d, J=14 Hz, 2H), 2.54 (s, 2H), 3.60 (s, 2H), 3.72 (s, 4H), 4.54 (s, 1H), 7.92 (d, J=5 Hz, 1H), 8.27 (d, J=6 Hz, 1H), 9.17 (s, 1H), 9.39 (s, 1H); MS (DCI/NH$_3$) m/z 314 (M+H)$^+$; Anal. C$_{17}$H$_{19}$N$_3$OS.2HCl.2.2H$_2$O: C, H, N.

Example 15

Benzothiazole-6-carboxylic acid (4r)-(1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and benzothiazole-6-carboxylic acid (Maybridge); yield 129 mg, 0.33 mmol (91%) according to methods A and C: $^1$H NMR (300 MHz, methanol-d4) δ 2.10-2.30 (m, 6H), 2.50 (s, 2H), 3.51 (d, J=12 Hz, 2H), 3.57 (s, 2H), 3.87 (d, J=13 Hz, 2H), 4.31 (s, 1H), 8.08 (dd, J=9, 2 Hz, 1H), 8.16 (d, J=9 Hz, 1H), 8.69 (d, J=2 Hz, 1H), 9.49 (s, 1H); MS (DCI/NH$_3$) m/z 314 (M+H)$^+$; Anal. C$_{17}$H$_{19}$N$_3$OS.2HCl.0.4H$_2$O: C, H, N.

Example 16

Benzothiazole-6-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and benzothiazole-6-carboxylic acid (Maybridge); yield 99 mg, 0.28 mmol (77%) according to methods A and C: $^1$H NMR (300 MHz, methanol-d4) δ 1.99 (d, J=14 Hz, 2H), 2.22 (s, 1H), 2.37 (d, J=14 Hz, 2H), 2.50 (s, 2H), 3.59 (s, 2H), 3.70 (s, 4H), 4.45 (s, 1H), 8.03 (dd, J=8, 2 Hz, 1H), 8.16 (d, J=8 Hz, 1H), 8.62 (d, J=2 Hz, 1H), 9.41 (s, 1H); MS (DCI/NH$_3$) m/z 314 (M+H)$^+$; Anal. C$_{17}$H$_{19}$N$_3$OS.HCl.0.3H$_2$O: C, H, N.

Example 17

2-Methyl-1H-benzoimidazole-5-carboxylic acid (4r)-(1-azatricyclo[3.3.1.1$^{3,7}$]dec-4-yl)-amide dihydrochloride

Prepared from (4r)-1-azatricyclo[3.3.1.1$^{3,7}$]dec-4-ylamine hydrochloride and 2-methyl-1H-benzimidazole-5-carboxylic acid (Acros) according to methods A and C; yield 83 mg, 0.21 mmol (58%): $^1$H NMR (300 MHz, methanol-d4) δ 2.02-2.31 (m, 5 H), 2.50 (s, 2H), 2.89 (s, 3H), 3.50 (d, J=13 Hz, 2H), 3.57 (s, 2H), 3.92 (d, J=13 Hz, 2 H), 4.32 (s, 1H), 7.82 (d, J=9 Hz, 1H), 8.11 (dd, J=9, 2 Hz, 1H), 8.33 (s, 1H), 8.57 (d, J=5 Hz, 1H); MS (DCI/NH$_3$) m/z 311 (M+H)$^+$; Anal. C$_{18}$H$_{22}$N$_4$O.2HCl.1.0H$_2$O: C, H, N.

Example 18

2-Methyl-1H-benzoimidazole-5-carboxylic acid (4s)-(1-azatricyclo[3.3.1.1$^{3,7}$]dec-4-yl)-amide dihydrochloride

Prepared from (4s)-1-azatricyclo[3.3.1.1$^{3,7}$]dec-4-ylamine hydrochloride and 2-methyl-1H-benzimidazole-5-carboxylic acid (Acros) according to methods A and C; yield 84 mg, 0.21 mmol (58%): $^1$H NMR (300 MHz, methanol-d4) δ 1.99 (d, J=13 Hz, 2 H), 2.30-2.46 (m, 3H), 2.51 (s, 2H), 2.90 (s, 3H), 3.59 (s, 2H), 3.69 (s, 4H), 4.45 (s, 1 H), 7.82 (dd, J=9, 1 Hz, 1H), 8.07 (dd, J=8, 1 Hz, 1H), 8.25 (dd, J=1, 1 Hz, 1H), 8.50 (d, J=5 Hz, 1H); MS (DCI/NH$_3$) m/z 311 (M+H)$^+$; Anal. C$_{18}$H$_{22}$N$_4$O.2HCl.1.0H$_2$O: C, H, N.

Example 19

2-Aminobenzothiazole-6-carboxylic acid (4r)-(1-azatricyclo[3.3.1.1$^{3,7}$]dec-4-yl)-amide bis(trifluoroacetate)

The protected amide[6-(1-azatricyclo[3.3.1.1$^{3,7}$]dec-4-yl-carbamoyl)-benzothiazol-2-yl)-carbamic acid tert-butyl ester] was prepared from (4r)-1-azatricyclo[3.3.1.1$^{3,7}$]dec-4-ylamine hydrochloride and 2-N-Boc-amino-4-benzothiazole-6-carboxylic acid (Astatech) according to method A. The resulting material was dissolved in dichloromethane (4 mL), treated with dichloromethane-trifluoroacetic acid (4 mL, 1:1), and stirred overnight. After concentrating the reaction mixture under a nitrogen stream, the residue was triturated with ether, and washed with ether and ethyl acetate to afford the title compound; yield 20 mg, 0.03 mmol (43%): $^1$H NMR (300 MHz, methanol-d4) δ 2.05-2.31 (m, 5H), 2.46 (s, 2H), 3.41-3.61 (m, 4H), 3.83 (d, J=13 Hz, 2H), 4.27 (s, 1H), 7.47 (d, J=8 Hz, 1H), 7.88 (d, J=8 Hz, 1H), 8.23 (s, 1H); MS (DCI/NH$_3$) m/z 329 (M+H)$^+$; Anal. C$_{17}$H$_{20}$N$_4$OS.2C$_2$HF$_3$O$_2$: C, H, N.

Example 20

5-Chlorothiophene-2-carboxylic acid (4r)-(1-azatricyclo[3.3.1.1$^{3,7}$]dec-4-yl)-amide hydrochloride

Prepared from (4r)-1-azatricyclo[3.3.1.1$^{3,7}$]dec-4-ylamine hydrochloride and 5-chlorothiophene-2-carboxylic acid (Aldrich) according to methods A and C; yield 62 mg, 0.19 mmol (59%): $^1$H NMR (300 MHz, methanol-d4) δ 2.05-2.26 (m, 5H), 2.43 (s, 2 H), 3.47 (d, J=13 Hz, 2H), 3.54 (s, 2H), 3.78 (d, J=13 Hz, 2H), 4.21 (t, J=3 Hz, 1H), 7.04 (d, J=4 Hz, 1H), 7.70 (d, J=4 Hz, 1H); MS (DCI/NH$_3$) m/z 297, 299 (M+H)$^+$; Anal. C$_{14}$H$_{17}$ClN$_2$OS.HCl: C, H, N.

Example 21

5-Chlorothiophene-2-carboxylic acid (4s)-(1-azatricyclo[3.3.1.1$^{3,7}$]dec-4-yl)-amide hydrochloride

Prepared from (4s)-1-azatricyclo[3.3.1.1$^{3,7}$]dec-4-ylamine hydrochloride and 5-chlorothiophene-2-carboxylic acid (Aldrich) according to methods A and C; yield 56 mg, 0.17 mmol (53%): $^1$H NMR (300 MHz, methanol-d4) δ 1.95 (d, J=14 Hz, 2H), 2.17 (s, 1 H), 2.29 (d, J=14 Hz, 2H), 2.43 (s, 2H), 3.55 (s, 2H), 3.64 (d, J=2 Hz, 4H), 4.34 (s, 1 H), 7.04 (d, J=4 Hz, 1H), 7.69 (d, J=4 Hz, 1H); MS (DCI/NH$_3$) m/z 297, 299 (M+H)$^+$; Anal. C$_{14}$H$_{17}$ClN$_2$OS.HCl.0.1H$_2$O: C, H, N.

Example 22

4-Phenylthiophene-2-carboxylic acid (4r)-(1-azatricyclo[3.3.1.1$^{3,7}$]dec-4-yl)-amide hydrochloride

Prepared from (4r)-1-azatricyclo[3.3.1.1$^{3,7}$]dec-4-ylamine hydrochloride and 4-phenylthiophene-2-carboxylic acid (Oakwood) according to methods A and C; yield 54 mg, 0.14 mmol (44%): $^1$H NMR (300 MHz, DMSO-d$_6$) δ 1.86-1.98 (m, 2H), 2.06 (d, J=13 Hz, 3H), 2.24 (s, 2H), 3.35 (d, J=9 Hz, 4H), 3.84 (d, J=13 Hz, 2H), 4.10-4.20 (m, 1H), 7.26-7.36 (m, 1H), 7.43 (t, J=7 Hz, 2H), 7.69-7.78 (m, 2H), 8.08 (d, J=1 Hz, 1H), 8.45 (d, J=6 Hz, 1H), 8.54 (d, J=1 Hz, 1H); MS (DCI/NH$_3$) m/z 339 (M+H)$^+$; Anal. C$_{20}$H$_{22}$N$_2$OS.HCl.0.07H$_2$O: C, H, N.

Example 23

4-Phenylthiophene-2-carboxylic acid (4s)-(1-azatricyclo[3.3.1.1$^{3,7}$]dec-4-yl)-amide hydrochloride

Prepared from (4s)-1-azatricyclo[3.3.1.1$^{3,7}$]dec-4-ylamine hydrochloride and 4-phenylthiophene-2-carboxylic acid (Oakwood) according to methods A and C; yield 65 mg, 0.17 mmol (53%): $^1$H NMR (300 MHz, methanol-d4) δ 1.98 (d, J=14 Hz, 2H), 2.20 (s, 1H), 2.37 (d, J=14 Hz, 2H), 2.48 (s, 2H), 3.57 (s, 2H), 3.67 (d, J=1 Hz, 4H), 4.40 (s, 1H), 7.26-7.36 (m, 1H), 7.42 (t, J=7 Hz, 2H), 7.65-7.74 (m, 2H), 7.89 (d, J=1 Hz, 1H), 8.27 (d, J=2 Hz, 1H); MS (DCI/NH$_3$) m/z 339 (M+H)$^+$; Anal. C$_{20}$H$_{22}$N$_2$OS.HCl.0.5H$_2$O: C, H, N.

Example 24

5-Phenylthiophene-2-carboxylic acid (4r)-(1-azatricyclo[3.3.1.1$^{3,7}$]dec-4-yl)-amide hydrochloride

Prepared from (4r)-1-azatricyclo[3.3.1.1$^{3,7}$]dec-4-ylamine hydrochloride and 5-phenylthiophene-2-carboxylic acid (Maybridge) according to methods A and C; yield 62 mg, 0.17 mmol (53%): $^1$H NMR (300 MHz, methanol-d4) δ 2.08-2.27 (m, 5H), 2.47 (s, 2H), 3.48 (d, J=13 Hz, 2H), 3.55 (s, 2H), 3.81 (d, J=13 Hz, 2H), 4.25 (t, J=3 Hz, 1H), 7.32-7.47 (m, 4H), 7.65-7.71 (m, 2H), 7.83 (d, J=4 Hz, 1H); MS (DCI/NH$_3$) m/z 339 (M+H)$^+$; Anal. C$_{20}$H$_{22}$N$_2$OS.HCl: C, H, N.

Example 25

5-Phenylthiophene-2-carboxylic acid (4s)-(1-azatricyclo[3.3.1.1$^{3,7}$]dec-4-yl)-amide hydrochloride

Prepared from (4s)-1-azatricyclo[3.3.1.1$^{3,7}$]dec-4-ylamine hydrochloride and 5-phenylthiophene-2-carboxylic acid (Maybridge) according to methods A and C; yield 67 mg, 0.18 mmol (82%): $^1$H NMR (300 MHz, methanol-d4) δ 1.97 (d, J=14 Hz, 2H), 2.20 (s, 1H), 2.33 (d, J=14 Hz, 2H), 2.48 (s, 2H), 3.57 (s, 2H), 3.67 (d, J=2 Hz, 4H), 4.39 (s, 1H), 7.32-7.47 (m, 4H), 7.66-7.72 (m, 2H), 7.83 (d, J=4 Hz, 1H); MS (DCI/NH$_3$) m/z 339 (M+H)$^+$; Anal. $C_{20}H_{22}N_2OS$·HCl: C, H, N.

Example 26

5-(Pyridin-2-yl)-thiophene-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 5-(2-pyridyl)thiophene-2-carboxylic acid (Maybridge) according to methods A and C; yield 35 mg, 0.09 mmol (43%): $^1$H NMR (300 MHz, methanol-d4) δ 2.07-2.29 (m, 5H), 2.48 (s, 2H), 3.49 (d, J=12 Hz, 2H), 3.56 (s, 2H), 3.83 (d, J=13 Hz, 2H), 4.26 (s, 1H), 7.29-7.39 (m, 1H), 7.71 (d, J=4 Hz, 1H), 7.83-7.91 (m, 3H), 8.50-8.56 (m, 1H); MS (DCI/NH$_3$) m/z 340 (M+H)$^+$; Anal. $C_{19}H_{21}N_3OS$·HCl·0.5H$_2$O: C, H, N.

Example 27

5-(Pyridin-2-yl)-thiophene-2-carboxylic acid (4s)-(1-azatricyclo[3.3.1.1$^{3,7}$]dec-4-yl)-amide dihydrochloride Prepared from (4s)-1-azatricyclo[3.3.1.1$^{3,7}$]dec-4-ylamine hydrochloride and 5-(2-pyridyl)thiophene-2-carboxylic acid (Maybridge) according to methods A and C; yield 49 mg, 0.14 mmol (66%): $^1$H NMR (300 MHz, methanol-d4) δ 1.98 (d, J=14 Hz, 2H), 2.21 (s, 1H), 2.34 (d, J=14 Hz, 2H), 2.50 (s, 2H), 3.58 (s, 2H), 3.68 (s, 4H), 4.41 (s, 1H), 7.75 (dt, J=7, 6, 1 Hz, 1H), 7.92 (d, J=4 Hz, 1H), 8.00 (d, J=4 Hz, 1H), 8.21 (d, J=8 Hz, 1H), 8.34 (dt, J=8, 2 Hz, 1H), 8.69 (d, J=5 Hz, 1H); MS (DCI/NH$_3$) m/z 340 (M+H)$^+$; Anal. $C_{21}H_{21}F_3N_2O_2$·2HCl·0.2H$_2$O·0.1C$_4$H$_8$O$_2$: C, H, N.

Example 28

2,2'-Bithiophene-5-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 2,2'-bithiophene-5-carboxylic acid (Acros) according to methods A and C; yield 142 mg, 0.37 mmol (93%): $^1$H NMR (300 MHz, methanol-d4) δ 2.06-2.27 (m, 5H), 2.46 (s, 2H), 3.49 (d, J=13 Hz, 2H), 3.55 (s, 2H), 3.82 (d, J=13 Hz, 2H), 4.24 (s, 1H), 7.08 (dd, J=5, 4 Hz, 1H), 7.24 (d, J=4 Hz, 1H), 7.35 (dd, J=4, 1 Hz, 1H), 7.43 (dd, J=5, 1 Hz, 1H), 7.79 (d, J=4 Hz, 1H); MS (DCI/NH$_3$) m/z 345 (M+H)$^+$; Anal. $C_{18}H_{20}N_2OS_2$·HCl: C, H, N.

Example 29

2,2'-Bithiophene-5-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 2,2'-bithiophene-5-carboxylic acid (Acros) according to methods A and C; yield 105 mg, 0.27 mmol (76%): $^1$H NMR (300 MHz, methanol-d4) δ 1.97 (d, J=14 Hz, 2H), 2.20 (s, 1H), 2.32 (d, J=14 Hz, 2H), 2.47 (s, 2H), 3.56 (s, 2H), 3.66 (s, 4H), 4.37 (s, 1H), 7.08 (dd, J=5, 4 Hz, 1H), 7.24 (d, J=4 Hz, 1H), 7.35 (dd, J=4, 1 Hz, 1H), 7.43 (dd, J=5, 1 Hz, 1H), 7.78 (d, J=4 Hz, 1H); MS (DCI/NH$_3$) m/z 345 (M+H)$^+$; Anal. $C_{18}H_{20}N_2OS_2$·HCl: C, H, N.

Example 30

5-(3-Trifluoromethylphenyl)-furan-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 5-[3-(trifluoromethyl)phenyl]-2-furoic acid (Aldrich) according to methods A and C; yield 29 mg, 0.07 mmol (31%): $^1$H NMR (300 MHz, methanol-d4) δ 2.09-2.30 (m, 5H), 2.52 (s, 2H), 3.50 (d, J=13 Hz, 2H), 3.57 (s, 2H), 3.83 (d, J=13 Hz, 2H), 4.28 (s, 1H), 7.12 (d, J=4 Hz, 1H), 7.34 (d, J=4 Hz, 1H), 7.63-7.69 (m, 2H), 8.10-8.18 (m, 1H), 8.24 (s, 1H); MS (DCI/NH$_3$) m/z 391 (M+H)$^+$; Anal. $C_{21}H_{21}F_3N_2O_2$·HCl·0.9H$_2$O: C, H, N.

Example 31

5-(3-Trifluoromethylphenyl)-furan-2-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 5-[3-(trifluoromethyl)phenyl]-2-furoic acid (Aldrich) according to methods A and C; yield 44 mg, 0.11 mmol (51%): $^1$H NMR (300 MHz, methanol-d4) δ 1.99 (d, J=14 Hz, 2H), 2.22 (s, 1H), 2.34 (d, J=14 Hz, 2H), 2.52 (s, 2H), 3.58 (s, 2H), 3.69 (s, 4H), 4.43 (s, 1H), 7.12 (d, J=4 Hz, 1H), 7.34 (d, J=4 Hz, 1H), 7.64-7.69 (m, 2H), 8.11-8.17 (m, 1H), 8.24 (s, 1H); MS (DCI/NH$_3$) m/z 391 (M+H)$^+$; Anal. $C_{21}H_{21}F_3N_2O_2$·HCl: C, H, N.

Example 32

5-(2-Nitrophenyl)-furan-2-carboxylic acid (4r)-1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 542-nitrophenyl)-2-furoic acid (Aldrich) according to methods A and C; yield 87 mg, 0.21 mmol (58%): $^1$H NMR (300 MHz, methanol-d4) δ 2.05-2.28 (m, 5H), 2.45 (s, 2H), 3.50 (s, 1H), 3.52-3.60 (m, 3H), 3.77 (d, J=13 Hz, 2H), 4.26 (s, 1H), 6.91 (d, J=4 Hz, 1H), 7.29 (d, J=3 Hz, 1H), 7.62 (dt, J=8, 2 Hz, 1H), 7.74 (dt, J=8, 1 Hz, 1H), 7.85 (dd, J=8, 1 Hz, 1H), 7.94 (dd, J=8, 1 Hz, 1H); MS (DCI/NH$_3$) m/z 368 (M+H)$^+$; Anal. $C_{20}H_{21}N_3O_4$·HCl·0.7H$_2$O: C, H, N.

Example 33

5-(2-Nitrophenyl)-furan-2-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 542-nitrophenyl)-2-furoic acid (Aldrich) according to methods A and C; yield 86 mg, 0.21 mmol (59%): $^1$H NMR (300 MHz, methanol-d4) δ 2.01 (d, J=13 Hz, 2H), 2.19-2.37 (m, 3H), 2.43 (s, 2H), 3.58 (s, 2H), 3.67 (s, 4H), 4.42 (s, 1H), 6.97 (d, J=4 Hz, 1H), 7.28 (d, J=3 Hz, 1H), 7.62 (dt, J=8, 1 Hz, 1H), 7.73 (dt, J=8, 1 Hz, 1H), 7.82 (dd, J=8, 1 Hz, 1H), 7.93 (dd, J=8, 1 Hz, 1H); MS (DCI/NH$_3$) m/z 368 (M+H)$^+$; Anal. $C_{20}H_{21}N_3O_4$·HCl·0.2H$_2$O: C, H, N.

Example 34

2-(Pyridin-4-yl)-thiazole-2-carboxylic acid (4r)-(1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and 2-(4-pyridyl)-1,3-thiazole-4-carboxylic acid (Maybridge) according to methods A and C; yield 84 mg, 0.19 mmol (54%): $^1$H NMR (300 MHz, methanol-d4) δ 2.03 (d, J=14 Hz, 2H), 2.24 (s, 1H), 2.33 (d, J=14 Hz, 2H), 2.53 (s, 2H), 3.60 (s, 2H), 3.72 (s, 4H), 4.50 (s, 1 H), 8.40 (d, J=6 Hz, 1H), 8.68 (s, 1H), 8.69-8.77 (m, 2H), 8.97 (d, J=7 Hz, 2H); MS (DCI/NH$_3$) m/z 341(M+H)$^+$; Anal. C$_{18}$H$_{20}$4OS.2HCl.1.2H$_2$O: C, H, N.

Example 35

2-(Pyridin-4-yl)-thiazole-2-carboxylic acid (4s)-(1-azatricyclo[3.3.1.1$^{3,7}$]dec-4-yl)-amide dihydrochloride Prepared from (4s)-1-azatricyclo[3.3.1.1$^{3,7}$]dec-4-ylamine hydrochloride and 2-(4-pyridyl)-1,3-thiazole-4-carboxylic acid (Maybridge) according to methods A and C; yield 103 mg, 0.22 mmol (62%): $^1$H NMR (300 MHz, methanol-d4) δ 2.03 (d, J=15 Hz, 2H), 2.24 (s, 1H), 2.33 (d, J=14 Hz, 2H), 2.53 (s, 2H), 3.60 (s, 2H), 3.71 (s, 4H), 4.50 (s, 1H), 8.40 (d, J=6 Hz, 1H), 8.70 (s, 1H), 8.72-8.80 (m, 2H), 8.94-9.04 (m, 2H); MS (DCI/NH$_3$) m/z 341 (M+H)$^+$; Anal. C$_{18}$H$_{20}$N$_4$OS.2HCl.2.75H$_2$O: C, H, N.

Example 36

2-(Thiophen-2-yl)-thiazole-4-carboxylic acid (4r)-1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and 2-(2-thienyl)-1,3-thiazole-4-carboxylic acid (Maybridge) according to methods A and C; yield 103 mg, 0.25 mmol (62%): $^1$H NMR (300 MHz, methanol-d4) δ 2.04-2.32 (m, 3H), 2.51 (s, 2H), 2.51 (s, 2H), 3.46-3.62 (m, 4H), 3.82 (d, J=13 Hz, 2H), 4.29 (s, 1H), 7.18 (dd, J=5, 4 Hz, 1H), 7.65 (dd, J=5, 1 Hz, 1H), 7.64 (dd, J=5, 1 Hz, 1H), 7.72 (dd, J=4, 1 Hz, 1H), 8.21 (s, 1H); MS (DCI/NH$_3$) m/z 346 (M+H)$^+$; Anal. C$_{17}$H$_{19}$N$_3$OS$_2$.2HCl: C, H, N.

Example 37

5-(Thiophen-2-yl)-1H-pyrazole-3-carboxylic acid (4r)-(1-azatricyclo[3.3.1.1$^{3,7}$]dec-4-yl)-amide dihydrochloride Prepared from (4r)-1-azatricyclo[3.3.1.1$^{3,7}$]dec-4-ylamine hydrochloride and 3-(2-thienyl)-1H-pyrazole-5-carboxylic acid (Specs) according to methods A and C; yield 34 mg, 0.08 mmol (33%): $^1$H NMR (300 MHz, methanol-d4) δ 2.09-2.29 (m, 6H), 2.45 (s, 2H), 3.49 (d, J=13 Hz, 2H), 3.56 (s, 2H), 3.83 (d, J=13 Hz, 2H), 4.29 (s, 1H), 7.02 (s, 1H), 7.12 (dd, J=5, 4 Hz, 1H), 7.43 (dd, J=4, 1 Hz, 1H), 7.48 (dd, J=5, 1 Hz, 1H); MS (DCI/NH$_3$) m/z 329 (M+H)$^+$; Anal. C$_{17}$H$_{20}$N$_4$OS.2HCl.0.15H$_2$O.0.05C$_4$H$_8$O$_2$: C, H, N.

Example 38

N-[(4r)-1-Azatricyclo[3.3.1.1$^{3,7}$]dec-4-yl]-4-(thiophen-2-yl)-benzamide tosylate Prepared from (4r)-1-azatricyclo[3.3.1.1$^{3,7}$]dec-4-ylamine hydrochloride and 4-(2-thienyl)benzoic acid (Maybridge) according to methods A and C; yield 156 mg, 0.30 mmol (75%): $^1$H NMR (300 MHz, methanol-d4) δ 2.08-2.27 (m, 6H), 2.35 (s, 3H), 2.47 (s, 2H), 3.49 (d, J=12 Hz, 2H), 3.56 (s, 2H), 3.84 (d, J=13 Hz, 2H), 4.27 (s, 1H), 7.13 (t, J=5, 3 Hz, 1H), 7.21 (d, J=9 Hz, 2H), 7.46 (d, J=5 Hz, 1H), 7.51 (d, J=2 Hz, 1H), 7.66-7.76 (m, 4H), 7.90 (d, J=9 Hz, 2H); MS (DCI/NH$_3$) m/z 339 (M+H)$^+$; Anal. C$_{20}$H$_{22}$N$_2$OS.C$_7$H$_8$O$_3$S.0.25H$_2$O: C, H, N.

Example 39

N-[(4s)-1-Azatricyclo[3.3.1.1$^{3,7}$]dec-4-yl]-4-(thiophen-2-yl)-benzamide tosylate Prepared from (4s)-1-azatricyclo[3.3.1.1$^{3,7}$]dec-4-ylamine hydrochloride and 4-(2-thienyl)benzoic acid (Maybridge) according to methods A and C; yield 133 mg, 0.26 mmol (65%): $^1$H NMR (300 MHz, methanol-d4) δ 1.96 (d, J=13 Hz, 2H), 2.19 (s, 1H), 2.28-2.39 (m, 5H), 2.47 (s, 2H), 3.57 (s, 2H), 3.67 (s, 4H), 4.40 (s, 1H), 7.13 (dd, J=5, 4 Hz, 1H), 7.19-7.25 (m, 2H), 7.46 (dd, J=5, 1 Hz, 1H), 7.51 (dd, J=4, 1 Hz, 1H), 7.67-7.79 (m, 4H), 7.87 (d, J=8 Hz, 1H); MS (DCI/NH$_3$) m/z 339 (M+H)$^+$; Anal. C$_{20}$H$_{22}$N$_2$OS.C$_7$H$_8$O$_3$S.0.35H$_2$O: C, H, N.

Example 40

N-[(4r)-1-Azatricyclo[3.3.1.1$^{3,7}$]dec-4-yl]-3,4-dichlorobenzamide hydrochloride Prepared from (4r)-1-azatricyclo[3.3.1.1$^{3,7}$]dec-4-ylamine hydrochloride and 3,4-dichlorobenzoic acid (Aldrich) according to methods A and C; yield 39 mg, 0.10 mmol (49%): $^1$H NMR (300 MHz, methanol-d4) δ 2.06-2.27 (m, 6H), 2.46 (s, 2H), 3.48 (d, J=12 Hz, 2H), 3.55 (s, 2H), 3.81 (d, J=13 Hz, 2H), 4.25 (s, 1H), 7.65 (d, J=8 Hz, 1H), 7.80 (dd, 1H), 8.07 (d, J=2 Hz, 1H); MS (DCI/NH$_3$) m/z 325 (M+H)$^+$; Anal. C$_{16}$H$_{18}$Cl$_2$N$_2$O.HCl.0.4HCl.0.15C$_4$H$_8$O$_2$: C, H, N.

Example 41

N-[(4s)-1-Azatricyclo[3.3.1.1$^{3,7}$]dec-4-yl]-3,4-dichlorobenzamide hydrochloride Prepared from (4s)-1-azatricyclo[3.3.1.1$^{3,7}$]dec-4-ylamine hydrochloride and 3,4-dichlorobenzoic acid (Aldrich) according to methods A and C; yield 49 mg, 0.15 mmol (69%): $^1$H NMR (300 MHz, methanol-d4) δ 1.96 (d, J=14 Hz, 2H), 2.20 (s, 1H), 2.32 (d, J=14 Hz, 2H), 2.46 (s, 2H), 3.57 (s, 2H), 3.67 (s, 4H), 4.39 (s, 1H), 7.65 (d, J=8 Hz, 1H), 7.77 (dd, J=8, 2 Hz, 1H), 8.02 (d, J=2 Hz, 1H); MS (DCI/NH$_3$) m/z 325 (M+H)$^+$; Anal. C$_{16}$H$_{18}$Cl$_2$N$_2$O.HCl: C, H, N.

Example 42

N-[(4r)-1-Azatricyclo[3.3.1.1$^{3,7}$]dec-4-yl]-4-chlorobenzamide

Prepared from (4r)-1-azatricyclo[3.3.1.1$^{3,7}$]dec-4-ylamine hydrochloride and 4-chlorobenzoic acid (Aldrich) according to method A; yield 29 mg, 0.07 mmol (33%): $^1$H NMR (300 MHz, methanol-d4) δ 2.06-2.30 (m, 5H), 2.45 (s, 2H), 3.48 (d, J=12 Hz, 2H), 3.55 (s, 2H), 3.80 (d, J=12 Hz, 2H), 4.25 (s, 1H), 7.49 (d, J=9 Hz, 2H), 7.86 (d, J=9 Hz, 2H); MS (DCI/NH$_3$) m/z 291 (M+H)$^+$; Anal. C$_{16}$H$_{19}$Cl$_2$N$_2$O.HCl.0.45HCl: C, H, N.

Example 43

N-[(4s)-1-Azatricyclo[3.3.1.1$^{3,7}$]dec-4-yl]-4-chlorobenzamide hydrochloride

Prepared from (4s)-1-azatricyclo[3.3.1.1$^{3,7}$]dec-4-ylamine hydrochloride and 4-chlorobenzoic acid (Aldrich) according to methods A and C; yield 49 mg, 0.17 mmol (63%): $^1$H NMR (300 MHz, methanol-d4) δ 1.96 (d, J=14 Hz, 2H), 2.20 (s, 1H), 2.32 (d, J=14 Hz, 2H), 2.46 (s, 2H), 3.57 (s, 2H), 3.67 (s, 4H), 4.39 (s, 1H), 7.49 (d, J=8 Hz, 2H), 7.83 (d, J=8 Hz, 2H); MS (DCI/NH$_3$) m/z 291 (M+H)$^+$; Anal. C$_{16}$H$_{19}$ClN$_2$O.HCl: C, H, N.

Example 44

N-[(4s)-1-Azatricyclo[3.3.1.1$^{3,7}$]dec-4-yl]-3-chlorobenzamide

Prepared from (4s)-1-azatricyclo[3.3.1.1$^{3,7}$]dec-4-ylamine and 3-chlorobenzoic acid (Aldrich) according to method B; $^1$H NMR (500 MHz, methanol-d4) δ 1.84-2.05 (m, 5H), 2.11 (s, 1H), 2.29 (s, 1H), 2.32 (d, J=14 Hz, 2H), 3.47-3.53 (m, 2H), 3.62-3.74 (m, 1H), 3.77-3.88 (m, 1H), 4.38 (s, 1H), 7.43-7.52 (m, 1H), 7.54-7.61 (m, 1H), 7.73-7.80 (m, 1H), 7.78-7.88 (m, 1H); MS (APCI/NH$_3$) m/z 291 (M+H)$^+$.

Example 45

N-[(4s)-1-Azatricyclo[3.3.1.1$^{3,7}$]dec-4-yl]-2,3-dichlorobenzamide

Prepared from (4s)-1-azatricyclo[3.3.1.1$^{3,7}$]dec-4-ylamine and 2,3-dichlorobenzoic acid (Aldrich) according to method B; $^1$H NMR (500 MHz, methanol-d4) δ 1.91-1.99 (m, 6H), 2.07 (d, 1H), 2.26 (d, J=13 Hz, 2H), 2.35 (s, 2H), 3.44-3.52 (m, 2H), 3.77-3.89 (m, 1H), 4.43 (s, 1H), 7.36-7.42 (m, 2H), 7.63 (dd, J=6, 4 Hz, 1H); MS (APCI/NH$_3$) m/z 325 (M+H)$^+$.

Example 46

N-[(4s)-1-Azatricyclo[3.3.1.1$^{3,7}$]dec-4-yl]-2,4-dichlorobenzamide

Prepared from (4s)-1-azatricyclo[3.3.1.1$^{3,7}$]dec-4-ylamine and 2,4-dichlorobenzoic acid (Aldrich) according to method B; $^1$H NMR (500 MHz, methanol-d4) δ 1.91-1.99 (m, 3H), 2.04 (s, 1H), 2.21-2.33 (m, 4H), 3.44 (s, 2H), 3.55 (s, 4H), 4.41 (s, 1H), 7.41-7.49 (m, 2H), 7.54-7.59 (m, 1H); MS (APCI/NH$_3$) m/z 325 (M+H)$^+$.

Example 47

N-[(4s)-1-Azatricyclo[3.3.1.1$^{3,7}$]dec-4-yl]-4-fluorobenzamide

Prepared from (4s)-1-azatricyclo[3.3.1.1$^{3,7}$]dec-4-ylamine and 4-fluorobenzoic acid (Aldrich) according to method B; $^1$H NMR (500 MHz, methanol-d4) δ 1.91-2.04 (m, 4H), 2.12 (s, 1H), 2.31 (d, J=14 Hz, 2H), 2.38 (s, 1H), 3.49 (s, 1H), 3.59 (s, 3H), 3.73 (s, 1H), 3.77-3.89 (m, 1H), 4.38 (s, 1H), 7.20 (t, J=9 Hz, 2H), 7.90 (dd, J=9, 5 Hz, 2H); MS (APCI/NH$_3$) m/z 275 (M+H)$^+$.

Example 48

N-[(4s)-1-Azatricyclo[3.3.1.1$^{3,7}$]dec-4-yl]-3-fluorobenzamide

Prepared from (4s)-1-azatricyclo[3.3.1.1$^{3,7}$]dec-4-ylamine and 3-fluorobenzoic acid (Aldrich) according to method B; $^1$H NMR (500 MHz, methanol-d4) δ 1.88-1.98 (m, 3H), 2.03 (s, 1H), 2.26-2.33 (m, 4H), 3.42 (s, 2H), 3.48-3.56 (m, 4H), 4.37 (s, 1H), 7.27-7.32 (m, 1H), 7.44-7.53 (m, 1H), 7.55-7.62 (m, 1H), 7.66 (d, J=8 Hz, 1H); MS (APCI/NH$_3$) m/z 275 (M+H)$^+$.

Example 49

N-[(4s)-1-Azatricyclo[3.3.1.1$^{3,7}$]dec-4-yl]-4-hydroxybenzamide

Prepared from (4s)-1-azatricyclo[3.3.1.1$^{3,7}$]dec-4-ylamine and 4-hydroxybenzoic acid (Aldrich) according to method B; $^1$H NMR (500 MHz, methanol-d4) δ 1.91-1.98 (m, 5H), 2.14 (s, 1H), 2.27-2.34 (m, 2H), 2.36-2.43 (m, 1H), 3.50 (s, 2H), 3.60 (s, 3 H), 4.36 (s, 1H), 6.70-6.98 (m, 2H), 7.56-7.82 (m, 2H); MS (APCI/NH$_3$) m/z 273 (M+H)$^+$.

Example 50

N-[(4s)-1-Azatricyclo[3.3.1.1$^{3,7}$]dec-4-yl]-3-hydroxybenzamide

Prepared from (4s)-1-azatricyclo[3.3.1.1$^{3,7}$]dec-4-ylamine and 3-hydroxybenzoic acid (Aldrich) according to method B; $^1$H NMR (500 MHz, methanol-d4) δ 1.96 (s, 3H), 2.12 (s, 1H), 2.29 (d, J=14 Hz, 2H), 2.38 (s, 2H), 3.49 (s, 2H), 3.59 (s, 3H), 3.74-3.91 (m, 1H), 4.36 (s, 1H), 6.90-7.06 (m, 1H), 7.18-7.25 (m, J=2 Hz, 1H), 7.24-7.31 (m, 2H); MS (APCI/NH$_3$) m/z 273 (M+H)$^+$.

Example 51

N-[(4s)-1-Azatricyclo[3.3.1.1$^{3,7}$]dec-4-yl]-4-methoxybenzamide

Prepared from (4s)-1-azatricyclo[3.3.1.1$^{3,7}$]dec-4-ylamine and 4-methoxybenzoic acid (Aldrich) according to method B; $^1$H NMR (500 MHz, methanol-d4) δ 1.92-1.99 (m, 4H), 2.12 (s, 1H), 2.31 (d, J=14 Hz, 2H), 2.39 (s, 1H), 3.50 (s, 2H), 3.60 (s, 3H), 3.84-3.87 (m, 3H), 4.37 (s, 1H), 6.97-7.03 (m, 2H), 7.75-7.88 (m, 2H); MS (APCI/NH$_3$) m/z 287 (M+H)$^+$.

Example 52

N-[(4s)-1-Azatricyclo[3.3.1.1$^{3,7}$]dec-4-yl]-3-methoxybenzamide

Prepared from (4s)-1-azatricyclo[3.3.1.1$^{3,7}$]dec-4-ylamine and 3-methoxybenzoic acid (Aldrich) according to method B; $^1$H NMR (500 MHz, methanol-d4) δ 2.30 (d, J=14 Hz, 6H), 2.40 (s, 2H), 3.49 (s, 2H), 3.60 (s, 3H), 3.79-3.89 (m, 4H), 4.38 (s, 1H), 7.13 (d, J=3 Hz, 1H), 7.33-7.44 (m, 3H); MS (APCI/NH$_3$) m/z 287 (M+H)$^+$.

Example 53

N-[(4s)-1-Azatricyclo[3.3.1.1$^{3,7}$]dec-4-yl]-2-ethoxybenzamide

Prepared from (4s)-1-azatricyclo[3.3.1.1$^{3,7}$]dec-4-ylamine and 2-ethoxybenzoic acid (Aldrich) according to method B; $^1$H NMR (500 MHz, methanol-d4) δ 1.53 (t, J=7 Hz, 3H), 1.94 (s, 1H), 2.02 (d, 2H), 2.11 (d, 1H), 2.20 (d, J=14 Hz, 2H), 2.32 (s, 2H), 3.48 (s, 2H), 3.59 (s, 4H), 4.28 (q, J=7 Hz, 2H), 4.47 (s, 1H), 7.06-7.10 (m, 1H), 7.17 (d, J=8 Hz, 1H), 7.48-7.53 (m, 1H), 7.96 (dd, J=8, 2 Hz, 1H); MS (APCI/NH$_3$) m/z 301 (M+H)$^+$.

Example 54

N-[(4s)-1-Azatricyclo[3.3.1.1$^{3,7}$]dec-4-yl]-3-trifluoromethoxybenzamide

Prepared from (4s)-1-azatricyclo[3.3.1.1$^{3,7}$]dec-4-ylamine and 3-trifluoromethoxybenzoic acid (Aldrich) according to method B; $^1$H NMR (500 MHz, methanol-d4) δ 1.96 (d, J=13 Hz, 2H), 2.12 (s, 1H), 2.31 (d, J=13 Hz, 2H), 2.40 (s, 2H), 3.50 (s, 2H), 3.60 (s, 4H), 4.40 (s, 1H), 7.45-7.51 (m, 1H), 7.56-7.62 (m, 1H), 7.74 (s, 1H), 7.82-7.87 (m, 1H); MS (APCI/NH$_3$) m/z 341 (M+H)$^+$.

Example 55

N-[(4s)-1-Azatricyclo[3.3.1.1$^{3,7}$]dec-4-yl]-4-phenoxybenzamide

Prepared from (4s)-1-azatricyclo[3.3.1.1$^{3,7}$]dec-4-ylamine and 4-phenoxybenzoic acid (Aldrich) according to method B; $^1$H NMR (500 MHz, methanol-d4) δ 1.95 (d, J=13 Hz, 2H), 2.11 (s, 1H), 2.31 (d, J=13 Hz, 2H), 2.38 (s, 2H), 3.49 (s, 2H), 3.59 (s, 4H), 4.38 (s, 1H), 7.00-7.09 (m, 4H), 7.17-7.23 (m, 1H), 7.38-7.44 (m, J=8, 8 Hz, 2H), 7.81-7.89 (m, 2H); MS (APCI/NH$_3$) m/z 349 (M+H)$^+$.

Example 56

N-[(4s)-1-Azatricyclo[3.3.1.1$^{3,7}$]dec-4-yl]-4-methylsulfanylbenzamide

Prepared from (4s)-1-azatricyclo[3.3.1.1$^{3,7}$]dec-4-ylamine and 4-(methylthio)benzoic acid (Aldrich) according to method B; $^1$H NMR (500 MHz, methanol-d4) δ 1.92-1.98 (m, 2H), 2.11 (s, 1H), 2.31 (d, J=14 Hz, 2H), 2.38 (s, 2H), 2.52 (s, 3H), 3.49 (s, 2H), 3.59 (s, 4H), 4.37 (s, 1H), 7.31-7.35 (m, 2H), 7.74-7.80 (m, 2H); MS (APCI/NH$_3$) m/z 287 (M+H)$^+$.

Example 57

Thiophene-2-carboxylic acid (4s)-(1-azatricyclo[3.3.1.1$^{3,7}$]dec-4-yl)-amide trifluoroacetate Prepared from (4s)-1-azatricyclo[3.3.1.1$^{3,7}$]dec-4-ylamine and 2-thiophenecarboxylic acid (Aldrich) according to method B; $^1$H NMR (500 MHz, methanol-d4) δ 1.93 (m, 2H), 2.15-2.36 (m, 3H), 2.46 (s, 1H), 2.70 (s, 1H), 3.56 (s, 1 H), 3.66 (s, 2H), 3.90 (s, 1H), 3.93 (d, 1H), 4.03 (d, 1H), 4.38 (s, 1H), 7.11-7.18 (m, 1H), 7.65-7.71 (m, 1H), 7.81-7.86 (m, 1H); MS (DCI/NH$_3$) m/z 263 (M+H)$^+$.

Example 58

5-Methylthiophene-2-carboxylic acid (4s)-(1-azatricyclo[3.3.1.1$^{3,7}$]dec-4-yl)-amide trifluoroacetate Prepared from (4s)-1-azatricyclo[3.3.1.1$^{3,7}$]dec-4-ylamine and 5-methyl-2-thiophenecarboxylic acid (Aldrich) according to method B; $^1$H NMR (500 MHz, methanol-d4) δ 1.92 (dd, J=26, 13 Hz, 2H), 2.15-2.34 (m, 3H), 2.44 (s, 1H), 2.51 (s, 3 H), 2.68 (s, 1H), 3.56 (s, 1H), 3.65 (s, 2H), 3.89 (s, 1H), 3.92 (d, 1H), 4.02 (d, 1H), 4.34 (s, 1H), 6.82 (dd, J=4, 1 Hz, 1H), 7.61-7.65 (m, 1H); MS (DCI/NH$_3$) m/z 277 (M+H)$^+$.

Example 59

3-Methylthiophene-2-carboxylic acid (4s)-(1-azatricyclo[3.3.1.1$^{3,7}$]dec-4-yl)-amide trifluoroacetate Prepared from (4s)-1-azatricyclo[3.3.1.1$^{3,7}$]dec-4-ylamine and 3-methyl-2-thiophenecarboxylic acid (Aldrich) according to method B; $^1$H NMR (500 MHz, methanol-d4) δ ppm 1.87-2.00 (m, J=26, 14 Hz, 2H), 2.15-2.29 (m, 3H), 2.44 (s, 1 H), 2.46-2.51 (m, J=3 Hz, 3H), 2.68 (s, 1H), 3.56 (s, 1H), 3.66 (d, J=2 Hz, 2H), 3.90 (s, 1H), 3.94 (d, 1H), 4.03 (d, 1H), 4.35-4.41 (m, 1H), 6.95 (d, J=5 Hz, 1H), 7.47 (d, J=5 Hz, 1H); MS (DCI/NH$_3$) m/z 277 (M+H)$^+$.

Example 60

Naphthalene-2-carboxylic acid (4s)-(1-azatricyclo[3.3.1.1$^{3,7}$]dec-4-yl)-amide Prepared from (4s)-1-azatricyclo[3.3.1.1$^{3,7}$]dec-4-ylamine and 2-naphthoic acid (Aldrich) according to method B; $^1$H NMR (500 MHz, methanol-d4) δ 1.94-2.03 (m, 3 H), 2.29-2.40 (m, 4H), 3.40 (s, 2H), 3.51 (s, 4H), 4.43 (s, 1H), 7.54-7.62 (m, 2H), 7.86-8.02 (m, 4H), 8.40 (d, J=1 Hz, 1H); MS (APCI/NH$_3$) m/z 307 (M+H)$^+$.

Example 61

1-Hydroxynaphthalene-2-carboxylic acid (4s)-(1-azatricyclo[3.3.1.1$^{3,7}$]dec-4-yl)-amide Prepared from (4s)-1-azatricyclo[3.3.1.1$^{3,7}$]dec-4-ylamine and 1-hydroxy-2-naphthoic acid (Aldrich) according to method B; $^1$H NMR (500 MHz, methanol-d4) δ 1.95-2.04 (m, 2H), 2.15-2.27 (m, 1H), 2.33-2.46 (m, 3H), 2.56-2.64 (m, 1H), 3.48-3.90 (m, 6H), 4.42-4.53 (m, 1H), 7.05-7.28 (m, 1H), 7.37-7.57 (m, 2H), 7.67-7.78 (m, 1H), 7.81-7.90 (m, 1H), 8.34-8.44 (m, 1H); MS (APCI/NH$_3$) m/z 323 (M+H)$^+$.

Example 62

Naphthalene-1-carboxylic acid (4s)-(1-azatricyclo[3.3.1.1$^{3,7}$]dec-4-yl)-amide Prepared from (4s)-1-azatricyclo[3.3.1.1$^{3,7}$]dec-4-ylamine and 1-naphthoic acid (Aldrich) according to method B; $^1$H NMR (500 MHz, methanol-d4) δ 1.94-2.71 (m, 7 H), 3.46-3.93 (m, 6H), 4.56 (s, 1H), 7.50-7.59 (m, 3H), 7.61-7.68

(m, 1H), 7.90-7.96 (m, 1H), 7.97-8.03 (m, 1H), 8.11-8.18 (m, 1H); MS (APCI/NH$_3$) m/z 307 (M+H)$^+$.

Example 63

6-Chloro-2H-chromene-3-carboxylic acid (4s)-(1-azatricyclo[3.3.1.1$^{3,7}$]dec-4-yl)-amide trifluoroacetate Prepared from (4s)-1-azatricyclo[3.3.1.1$^{3,7}$]dec-4-ylamine and 6-chloro-2H-1-benzopyran-3-carboxylic acid (Acros) according to method B; $^1$H NMR (500 MHz, methanol-d4) δ 1.84-2.00 (m, 2H), 2.14-2.67 (m, 5H), 3.51-3.72 (m, 4H), 3.86-4.08 (m, 2H), 4.28-4.33 (m, 1H), 4.95 (t, J=2 Hz, 2H), 6.82 (d, J=8 Hz, 1H), 7.17-7.27 (m, 3H); MS (DCI/NH$_3$) m/z 345 (M+H)$^+$.

Example 64

Benzo[1,3]dioxole-5-carboxylic acid (4s)-(1-azatricyclo[3.3.1.1$^{3,7}$]dec-4-yl)-amide Prepared from (4s)-1-azatricyclo[3.3.1.1$^{3,7}$]dec-4-ylamine and piperonylic acid (Aldrich) according to method B; $^1$H NMR (500 MHz, methanol-d4) δ 1.86-2.63 (m, 7H), 3.46-3.86 (m, 6H), 4.35 (s, 1H), 6.02-6.05 (m, 2H), 6.90 (d, J=8 Hz, 1H), 7.32 (d, J=2 Hz, 1H), 7.44 (dd, J=8, 2 Hz, 1H); MS (APCI/NH$_3$) m/z 301 (M+H)$^+$.

Example 65

2,3-Dihydrobenzo[1,4]dioxine-6-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 1,4-benzodioxan-6-carboxylic acid (Maybridge) according to methods A and C; yield 49 mg, 0.13 mmol (42%): $^1$H NMR (300 MHz, methanol-d4) δ 2.08-2.29 (m, 5H), 2.49 (s, 2H), 3.50 (d, J=13 Hz, 2H), 3.56 (s, 2H), 3.85 (d, J=13 Hz, 2H), 4.28 (s, 1H), 7.38-7.50 (m, 2H), 7.87-7.96 (m, 2H), 8.14 (d, J=1 Hz, 1H); MS (DCI/NH$_3$) m/z 315 (M+H)$^+$; Anal. C$_{18}$H$_{22}$N$_2$O$_3$.HCl.0.25NH$_4$OH: C, H, N.

Example 66

2,3-Dihydrobenzo[1,4]dioxine-6-carboxylic acid (4s)-(1-azatricyclo[3.3.1.1$^{3,7}$]dec-4-yl)-amide hydrochloride Prepared from (4s)-1-azatricyclo[3.3.1.1$^{3,7}$]dec-4-ylamine hydrochloride and 1,4-benzodioxan-6-carboxylic acid (Maybridge) according to methods A and C; yield 49 mg, 0.14 mmol (43%): $^1$H NMR (300 MHz, methanol-d4) δ 1.94 (d, J=13 Hz, 2H), 2.18 (s, 2 H), 2.30 (d, J=14 Hz, 2H), 2.44 (s, 2H), 3.55 (s, 1H), 3.65 (d, J=2 Hz, 4H), 4.24-4.32 (m, 4H), 4.35 (s, 1H), 6.90 (ddd, J=9, 1 Hz, 1H), 7.33-7.39 (m, 2H); MS (DCI/NH$_3$) m/z 315 (M+H)$^+$; Anal. C$_{18}$H$_{22}$N$_2$O$_3$.HCl.0.25H$_2$O: C, H, N.

Example 67

Furo[2,3-c]pyridine-5-carboxylic acid (1-aza-tricyclo[3.3.1.1$^{3,7}$]dec-4-yl)-amide Prepared from 4r-amino-1-azaadamantane hydrochloride and furo[2,3-c]pyridine-5-carboxylic acid (EP911335) according to methods A and C; yield 67 mg, 0.14 mmol (37%): $^1$H NMR (300 MHz, methanol-d4) δ 2.10-2.29 (m, 5H), 2.36 (s, 3H), 2.52 (s, 2 H), 3.51 (d, J=12.9 Hz, 2H), 3.57 (s, 2H), 3.92 (d, J=12.5 Hz, 2H), 4.35 (s, 1H), 7.20 (d, J=8.1 Hz, 2H), 7.29 (d, J=2.4 Hz, 1H), 7.67 (d, J=8.5 Hz, 2H), 8.44 (d, J=2.4 Hz, 1H), 8.81 (s, 1H), 9.16 (s, 1H). MS (DCI/NH$_3$) m/z 298 (M+H)$^+$; Anal. C$_{17}$H$_{19}$N$_3$O.1.5C$_7$H$_8$O$_3$S.1.65H$_2$O: C, H, N

Example 68

3-Methyl-benzofuran-2-carboxylic acid (1-aza-tricyclo[3.3.1.1$^{3,7}$]dec-4-yl)-amide Prepared from 4r-amino-1-azaadamantane hydrochloride and 3-methyl-benzofuran-2-carboxylic acid (Aldrich) according to methods A and C; yield 97 mg, 0.20 mmol (47%): $^1$H NMR (300 MHz, methanol-d4) δ 2.07-2.29 (m, 5H), 2.35 (s, 3H), 2.48 (s, 2H), 2.59 (s, 3H), 3.49 (d, J=12 Hz, 2H), 3.56 (s, 2H), 3.84 (d, J=12 Hz, 2H), 4.30 (s, 1H), 7.21 (d, J=8 Hz, 2H), 7.33 (t, J=7 Hz, 1H), 7.47 (t, J=7 Hz, 1H), 7.51-7.58 (m, 1H), 7.70 (d, J=8 Hz, 2H); MS (DCI/NH$_3$) m/z 311 (M+H)$^+$; Anal. C$_{19}$H$_{22}$N$_2$O$_2$.C$_7$H$_8$O$_3$S.0.25H$_2$O: C, H, N

Example 69

Furo[2,3-c]pyridine-5-carboxylic acid (1-aza-tricyclo[3.3.1.1$^{3,7}$]dec-4-yl)-amide Prepared from 4s-amino-1-azaadamantane hydrochloride and furo[2,3-c]pyridine-5-carboxylic acid (EP911335) according to methods A and C; yield 71 mg, 0.15 mmol (36%): $^1$H NMR (300 MHz, methanol-d4) δ 2.02 (d, J=13 Hz, 2H), 2.19-2.33 (m, 3H), 2.36 (s, 3H), 2.46 (s, 2H), 3.59 (s, 2H), 3.71 (s, 4H), 4.48 (s, 1H), 7.13 (d, J=2.4 Hz, 1H), 7.23 (d, J=8 Hz, 2H), 7.70 (d, J=8 Hz, 2H), 8.13 (d, J=2.4 Hz, 1H), 8.48 (s, 1H), 8.93 (s, 1H). MS (DCI/NH$_3$) m/z 298 (M+H)$^+$; Anal. C$_{17}$H$_{19}$N$_3$O.1.0C$_7$H$_8$O$_3$S.0.75H$_2$O: C, H, N

Example 70

2-Naphthoic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 2-naphthoic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.51-7.67 (m, 2H), 7.85-8.07 (m, 4H), 8.46 (s, 1H). MS (DCI/NH$_3$) m/z 308. Anal. Calculated for C$_{20}$H$_{22}$N$_2$O.HCl: C, 70.06; H, 6.76; N, 9.14. Found: C, 69.72; H, 6.58; N, 8.03.

Example 71

Benzofuran-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and benzofuran-2-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.29-7.38 (m, 1H), 7.44-7.52 (m, 1H), 7.57 (s, 1H), 7.61 (d, J=7.4 Hz, 1H), 7.74 (d, J=7.8

Hz, 1H). MS (DCI/NH$_3$) m/z 297. Anal. Calculated for C$_{18}$H$_{20}$N$_2$O$_2$.HCl: C, 64.96; H, 6.36; N, 8.42. Found: C, 64.51; H, 6.23; N, 8.14.

Example 72

Benzo[d][1,2,3]thiadiazole-5-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and benzo[d][1,2,3]thiadiazole-5-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 8.22 (d, J=8.5 Hz, 1H), 8.36 (d, J=8.5 Hz, 1H), 9.19 (s, 1H). MS (DCI/NH$_3$) m/z 315. Anal. Calculated for C$_{16}$H$_{18}$N$_4$OS.HCl: C, 54.77; H, 5.46; N, 15.97. Found: C, 53.27; H, 4.94; N, 15.47.

Example 73

Isoquinoline-3-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and isoquinoline-3-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.43 (d, J=8.8 Hz, 2H), 7.68 (d, J=8.8 Hz, 2H), 7.93 (d, J=1.4 Hz, 1H), 8.24 (d, J=1.7 Hz, 1H). MS (DCI/NH$_3$) m/z 308. Anal. Calculated for C$_{19}$H$_{21}$N$_3$O.HCl: C, 66.37; H, 6.45; N, 12.22. Found: C, 47.6; H, 5.89; N, 8.71.

Example 74

Benzo[c][1,2,5]thiadiazole-5-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and benzo[c][1,2,5]thiadiazole-5-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.90-8.51 (m, 1H), 8.98 (s, 1H), 9.57 (s, 1H). MS (DCI/NH$_3$) m/z 315. Anal. Calculated for C$_{16}$H$_{18}$N$_4$OS.HCl: C, 54.77; H, 5.46; N, 15.97. Found: C, 53.82; H, 5.31; N, 16.17.

Example 75

5-(2-Methylthiazol-4-yl)thiophene-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 5-(2-methylthiazol-4-yl)thiophene-2-carboxylic acid according to methods A and C. $^1$H NMR (300 MHz, methanol-d4) δ ppm 2.08-2.34 (m, 5H), 2.51 (s, 2H), 2.74 (s, 3H), 3.42-3.64 (m, 4H), 3.88 (d, J=12.5 Hz, 2H), 4.33 (s, 1H), 7.49 (d, J=4.1 Hz, 1H), 7.68 (s, 1 H), 7.79 (d, J=4.1 Hz, 1H). MS (DCI/NH$_3$) m/z 360.

Example 76

3-(Thiophen-2-yl)benzoic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 3-thiophen-2-yl)benzoic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.13 (dd, J=5.1, 3.73 Hz, 1H), 7.43 (dd, J=5.1, 1.0 Hz, 1H), 7.47-7.55 (m, 2H), 7.80 (dd, J=16.6, 8.1 Hz, 2H), 8.11 (t, J=1.7 Hz, 1H). MS (DCI/NH$_3$) m/z 339.

Example 77

Thieno[3,2-b]thiophene-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and thieno[3,2-b]thiophene-2-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.37 (d, J=5.1 Hz, 1H), 7.71 (d, J=5.1 Hz, 1H), 8.12 (s, 1H). MS (DCI/NH$_3$) m/z 319.

Example 78

Thieno[2,3-b]thiophene-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and thieno[2,3-b]thiophene-2-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.32 (d, J=5.4 Hz, 1H), 7.53-7.58 (m, 1H), 8.06 (s, 1 H). MS (DCI/NH$_3$) m/z 319. Anal. Calculated for C$_{16}$H$_{18}$N$_2$OS$_2$.HCl: C, 54.15; H, 5.40; N, 7.89. Found: C, 54.19; H, 5.25; N, 7.72.

Example 79

5-Chlorobenzofuran-2-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 5-chlorobenzofuran-2-carboxylic acid according to methods A and C. $^1$H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 6.43-6.48 (m, 1H), 6.52 (s, 1H), 6.57-6.62 (m, 1H), 6.76 (d, J=2.0 Hz, 1H). MS (DCI/NH$_3$) m/z 331.

Example 80

1H-Indazole-3-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 1H-indazole-3-carboxylic acid according to methods A and C. $^1$H NMR (300 MHz, methanol-d4) δ ppm 2.08-2.34 (m, 5H), 2.51 (s, 2H), 3.42-3.64 (m, 24H), 3.88 (d, J=12.5 Hz, 2H), 4.33 (s, 1H), 7.23-7.32 (m, 1H), 7.40-7.48 (m, 1H), 7.57-7.63 (m, 1 H), 8.20 (d, J=8.1 Hz, 1H). MS (DCI/NH$_3$) m/z 297.

Example 81

1H-Indazole-4-carboxylic acid (4r)-(1-azatricyclo[3.3.1.1$^{3,7}$]dec-4-yl)-amide hydrochloride Prepared from (4r)-1-azatricyclo[3.3.1.1$^{3,7}$]dec-4-ylamine hydrochloride and 1H-indazole-4-carboxylic acid according to methods A and C. ¹H NMR (300 MHz, methanol-d4) δ ppm 2.08-2.34 (m, 5H), 2.51 (s, 2H), 3.42-3.64 (m, 4H), 3.88 (d, J=12.5 Hz, 2H), 4.33 (s, 1H), 7.42-7.52 (m, 1H), 7.58-7.64 (m, 1H), 7.72 (d, J=8.5 Hz, 1H), 8.33 (s, 1H). MS (DCI/NH$_3$) m/z 297.

DETERMINATION OF BIOLOGICAL ACTIVITY

To determine the effectiveness of representative compounds of this invention as α7 nAChRs, the compounds of the invention were evaluated according to the [³H]-methyllycaconitine (MLA) binding assay, or the [³H]-DPPB binding assay, and considering the [³H]-cytisine binding assay, which were performed as described below.

[³H]-Cytisine Binding

Binding conditions were modified from the procedures described in Pabreza L A, Dhawan, S, Kellar K J, [³H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [³H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (–)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 µL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(1+[Ligand]/K$_D$).

[³H]-Methyllycaconitine (MLA) Binding

Binding conditions were similar to those for [³H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100-200 µg of protein, 5 nM [3H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20 scintillation cocktail (40 µL) was added to each well and radioactivity was determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(1+[Ligand]/K$_D$).

[³H]-DPPB Binding

[³H]-DPPB, [³H]-(S,S)-2,2-dimethyl-5-(6-phenyl-pyridazin-3-yl)-5-aza-2-azonia-bicyclo[2.2.1]heptane iodide, binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). Seven log-dilution concentrations of test compounds containing 100-200 µg of protein, and 0.5 nM [³H]-DPPB (62.8 Ci/mmol; R46V, Abbott Labs) were incubated in a final volume of 500 µl for 75 minutes at 4° C. in duplicate. Non-specific binding was determined in the presence of 10 µM methyllycaconitine. Bound radioactivity was collected on Millipore MultiScreen® harvest plates FB presoaked with 0.3% PEI using a Packard cell harvester, washed with 2.5 ml ice-cold buffer, and radioactivity was determined using a Packard TopCount Microplate beta counter. IC$_{50}$ values were determined by nonlinear regression in Microsoft® Excel or Assay Explorer. K$_i$ values were calculated from the IC$_{50}$s using the Cheng-Prusoff equation, where K$_i$=IC$_{50}$/(1+[Ligand]/K$_D$). [³H]-DPPB was obtained according to the preparation procedures described below.

[Methyl-³H]2,2-Dimethyl-5-(6-phenyl-pyridazin-3-yl)-5-aza-2-azonia-bicyclo[2.2.1]heptane; iodide Preparation

[Methyl-³H]2,2-dimethyl-5-(6-phenyl-pyridazin-3-yl)-5-aza-2-azonia-bicyclo[2.2.1]heptane; iodide used in the [³H]-DPPB binding assay above was prepared according to the following procedures.

Step 1: Preparation of t-Butyl(S,S)-5-(6-Phenyl-pyridazin-3-yl)-2,5-diaza-bicyclo[2.2.1]heptane-2-carboxylate Triethylamine (20 mL) was added to a suspension of t-butyl(S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated and the residue wa purified by column chromatography on silica gel, eluting with ethyl acetate, to provide additional product (0.41 g, total yield 3.41 g, 56%): MS (DCI/NH$_3$) m/z 353 (M+H)$^+$.

Step 2: Preparation of (S,S)-2-Methyl 5-(6-phenyl-pyridazin-3-yl)-2,5-diaza-bicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 h, and the brown solution was cooled to room temperature and concentrated under vacuum. The residue was purified by column chromatography on silica gel, eluting with CH$_2$Cl$_2$—CH$_3$OH—NH$_4$OH (95:5:1) to provide the title compound as an off-white solid (2.50 g, 96%): MS (DCI/NH$_3$) m/z 267 (M+H)$^+$.

Step 3: Preparation of [³H]-(S,S)-2,2-Dimethyl-5-(6-phenyl-pyridazin-3-yl)-5-aza-2-azonia-bicyclo[2.2.1]heptane iodide ([³H]-DPPB)

[³H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 μmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 ml acetonitrile:water:TFA (15:85:0.1). Approximately 0.9 mL per injection were made onto a Phenomenex Luna C18(2) column (5 micron, 250 mm×4.6 mm ID) using an Agilent HPLC system. [$^3$H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 mL/min. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 μL flow cell and a 3:1 ratio of Ultima-Flo M scintillation cocktail to HPLC mobile phase were used. The analyses were performed using a Phenomenex Luna C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

The radiochemical purity of [$^3$H]-DPPB was found to be >98%. The specific activity was determined to be 62.78 Ci/mmol by mass spectroscopy.

Other suitable radioligands are compounds of the formula (III):

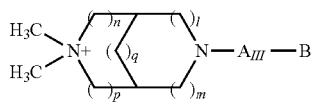

wherein:

m, n, and q each are independently 0, 1, or 2;

l and p each are independently 1 or 2;

the sum of l, m, n, p, and q is 3, 4, 5, or 6;

A$_{III}$ is selected from:

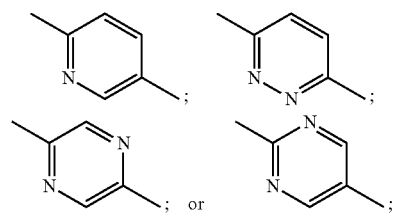

B is selected from substituted or unsubstituted phenyl. Phenyl groups can be unsubstituted or substituted with one, two, three, four, or five substituents independently selected from alkenyl, alkoxy, alkoxyalkyl, alkoxycarbonyl, alkyl, alkylcarbonyl, arylcarbonyl, alkylcarbonyloxy, alkylthio, alkynyl, carboxy, cyano, haloalkoxy, haloalkyl, halogen, hydroxy, hydroxyalkyl, mercapto, and nitro. Preferred compounds are those wherein the phenyl groups is 3,4-(methylenedioxy)phenyl or phenyl substituted with 0, 1, 2, or 3 substituents in the meta- or para-positions selected from alkenyl, alkoxy, alkoxyalkyl, alkoxycarbonyl, alkyl, alkylcarbonyl, arylcarbonyl, alkylcarbonyloxy, alkylthio, alkynyl, carboxy, cyano, haloalkoxy, haloalkyl, halogen, hydroxy, hydroxyalkyl, mercapto, and nitro.

Radiolabelled compounds of formula (III) can be prepared from tertiary amines of Formula (IV) described in U.S. patent application Ser. No. 10/666,884, filed Sep. 19, 2003, which published as US20050065178A1, and U.S. patent application Ser. No. 10/942,035, filed Sep. 16, 2004, which published as US20050101602A1 by treating a desired tertiary amine with [$^3$H]-methyl iodide as illustrated below and as described above in Steps 3-5.

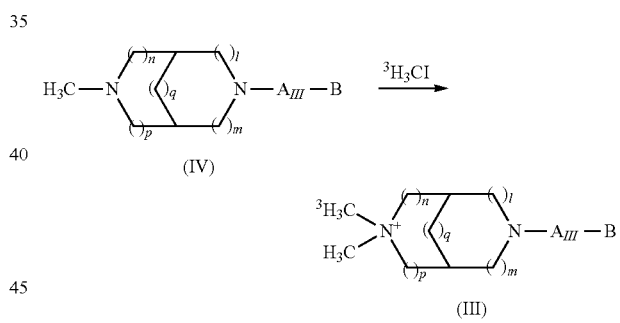

Methods for preparing compounds within the scope of formula (IV) are described in U.S. patent application Ser. No. 10/666,884 and U.S. patent application Ser. No. 10/942,035, both of which are incorporated by reference herein in their entirety.

Briefly, a bromide, 1,4-bromochloride, or 1,4-dichloride of a desired aromatic nitrogen ring represented by AIII is coupled with a desired diamine group under palladium coupling conditions, for example Pd(0) and base or Pd(0), 2,2'-bis(diphenylphosphino)-1,1'-binaphthyl (BINAP), and base. The product obtained is further coupled with a boronic acid of a desired substituted or unsubstituted phenyl group under suitable palladium coupling conditions, for example Pd(0) and base. Methods for preparing compounds of formula (IV) are further described in US20050065178A1, which published on Mar. 24, 2005, and US20050101602A1, which published on May 12, 2005.

The term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

Radiolabels can be incorporated into known compounds by a number of methods. Particularly suitable for providing radioligands of formula (III) are those wherein a $^{14}$CH$_3$ group can be incorporated in by reaction with $^{14}$CH$_3$I. The incorporation of $^{14}$CH$_3$I can be carried out according to a method such as that described in Step 3 above, substituting $^{14}$CH$_3$I for a $^{12}$C$^3$H$_3$I. For example, as shown below:

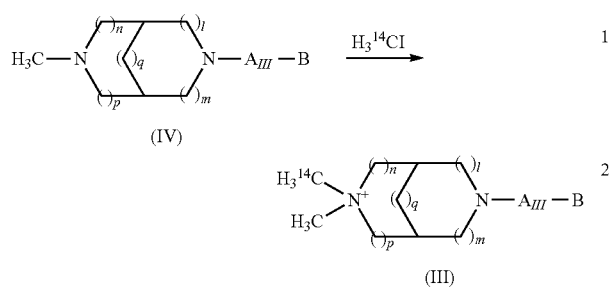

wherein l, m, n, p, q, A$_{III}$, and B are as defined above for compounds of formula (III). Methods of incorporating radiolabels into known compounds are well known to those skilled in the art of synthetic organic chemistry or medicinal chemistry.

Specific embodiments of radiolabelled compounds of formula (III) include, but are not limited to, the following:

[$^3$H]-(S,S)-2,2-dimethyl-5-(6-phenyl-pyridazin-3-yl)-5-aza-2-azonia-bicyclo[2.2.1]heptane, iodide (DPPB);

[$^3$H]-(R,R)-2,2-dimethyl-5-(6-phenyl-pyridazin-3-yl)-5-aza-2-azonia-bicyclo[2.2.1]heptane, iodide;

[$^3$H]-2,2-dimethyl-5-(6-phenyl-pyridazin-3-yl)-octahydro-pyrrolo[3,4-c]pyrrol-2-ium, iodide;

[$^3$H]-(1R,6S)-9,9-dimethyl-3-(6-phenyl-pyridazin-3-yl)-3-aza-9-azonia-bicyclo[4.2.1]nonane, iodide; and

[$^3$H]-(1S,6R)-9,9-dimethyl-3-(6-phenyl-pyridazin-3-yl)-3-aza-9-azonia-bicyclo[4.2.1]nonane, iodide.

[$^3$H]-(S,S)-2,2-dimethyl-5-(6-phenyl-pyridazin-3-yl)-5-aza-2-azonia-bicyclo[2.2.1]heptane, iodide is preferred.

Compounds of the invention had K$_i$ values of from about 1 nanomolar to about 10 micromolar when tested by the [$^3$H]-MLA assay, many having a K$_i$ of less than 1 micromolar. [$^3$H]-Cytisine binding values of compounds of the invention ranged from about 50 nanomolar to at least 100 micromolar. Preferred compounds typically exhibited greater potency at α7 receptors compared to α4β2 receptors. The determination of preferred compounds typically considered the K$_i$ value as measured by MLA assay in view of the K$_i$ value as measured by [$^3$H]-cytisine binding, such that in the formula D=K$_i$$^3$H-cytisine K$_{iMLA}$, D is greater than about 50. Alternatively, the K$_i$ value as measured by [$^3$H]-DPPB assay can be used in place of the K$_{iMLA}$ such that in the formula D'=K$_i$$^3$$_{H\text{-}cytisine}$/K$_{i[3H]\text{-}DPPB}$, D' is greater than about 50.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory, cytoprotection, gene transcription and disease modification.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

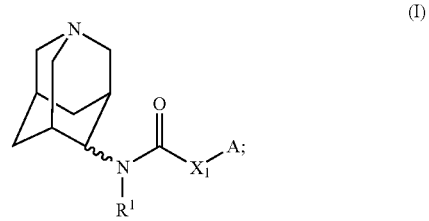

or a pharmaceutically acceptable salt or prodrug thereof, wherein

X$_1$ is a bond or is selected from the group consisting of —O—, —O-alkylene, —NR$_2$— and —NR$_2$-alkylene, wherein the oxygen atom of —O-alkylene and the nitrogen atom of —NR$_2$-alkylene is attached to the parent molecular moiety;

A is —Ar$_2$—Y—Ar$_3$;

Ar$_2$ is selected from the group consisting of aryl and heteroaryl, wherein Ar$_2$ is unsubstituted or substituted with a substituent selected from alkyl, haloalkyl and nitro;

Ar$_3$ is selected from the group consisting of aryl and heteroaryl, wherein Ar$_3$ is unsubstituted or substituted with a substituent selected from alkyl, haloalkyl and nitro;

Y is a bond or —O—; and

R$_1$, R$_2$ and R$_3$ are individually selected from the group consisting of hydrogen and C$_1$-C$_6$ alkyl.

2. The compound according to claim 1, wherein

X$_1$ is a bond;

Ar$_2$ is selected from the group consisting of phenyl, a 5 or 6 membered monocyclic heteroaryl ring and a bicyclic heteroaryl ring, wherein Ar$_2$ is substituted or unsubstituted wherein each substituent is independently selected from the group consisting of alkyl, haloalkyl, and nitro; and Ar$_3$ is selected from the group consisting of phenyl, a 5 or 6 membered monocyclic heteroaryl ring and a bicyclic heteroaryl ring, wherein Ar$_3$ is substituted or unsubstituted wherein each substituent is independently selected from the group consisting of alkyl, haloalkyl and nitro.

3. The compound according to claim 1, wherein

X$_1$ is a bond;

Ar$_2$ is selected from the group consisting of phenyl and a 5 or 6 membered monocyclic heteroaryl ring, wherein Ar$_2$ is substituted or unsubstituted wherein each substituent is independently selected from the group consisting of alkyl, haloalkyl and nitro; and Ar₃ is selected from the group consisting of phenyl, a 5 or 6 membered monocyclic heteroaryl ring and a bicyclic heteroaryl ring, wherein Ar₃ is substituted or unsubstituted wherein each substituent is independently selected from the group consisting of alkyl, haloalkyl and nitro.

4. The compound according to claim 1, wherein
$X_1$ is a bond;
$Ar_2$ is phenyl which is optionally substituted with 1, 2, 3, 4 or 5 substituents independently selected from the group consisting of alk alkyl, haloalkyl and nitro; and
$Ar_3$ is selected from the group consisting of phenyl, a 5 or 6 membered monocyclic heteroaryl ring and a bicyclic heteroaryl ring, wherein $Ar_3$ is substituted or unsubstituted wherein each substituent is independently selected from the group consisting of alkyl, haloalkyl and nitro.

5. The compound according to claim 1, wherein
$X_1$ is a bond;
$Ar_2$ is a 5 or 6 membered monocyclic heteroaryl ring which is optionally substituted with 1, 2, 3, 4 or 5 substituents independently selected from the group consisting of alkyl, haloalkyl and nitro; and
$Ar_3$ is selected from the group consisting of phenyl, a 5 or 6 membered monocyclic heteroaryl ring and a bicyclic heteroaryl ring, wherein $Ar_3$ is substituted or unsubstituted wherein each substituent is independently selected from the group consisting of alkyl, haloalkyl and nitro.

6. The compound according to claim 1, wherein
$X_1$ is a bond;
$Ar_2$ is a bicyclic heteroaryl ring which is optionally substituted with 1, 2, 3, 4 or 5 substituents independently selected from the group consisting of alkyl, haloalkyl and nitro; and
$Ar_3$ is selected from the group consisting of phenyl, a 5 or 6 membered monocyclic heteroaryl ring and a bicyclic heteroaryl ring, wherein $Ar_3$ is substituted or unsubstituted wherein each substituent is independently selected from the group consisting of alkyl, haloalkyl and nitro.

7. The compound selected from the group consisting of
4-phenylthiophene-2-carboxylic acid (4r)-(1-azatricyclo[3.3.1.1³,⁷]dec-4-yl)-amide;
4-phenylthiophene-2-carboxylic acid (4s)-(1-azatricyclo[3.3.1.1³,⁷]dec-4-yl)-amide;
5-phenylthiophene-2-carboxylic acid (4r)-(1-azatricyclo[3.3.1.1³,⁷]dec-4-yl)-amide;
5-phenylthiophene-2-carboxylic acid (4s)-(1-azatricyclo[3.3.1.1³,⁷]dec-4-yl)-amide;
5-(pyridin-2-yl)-thiophene-2-carboxylic acid (4r)-(1-azatricyclo[3.3.1.1³,⁷]dec-4-yl)-amide;
5-(pyridin-2-yl)-thiophene-2-carboxylic acid (4s)-(1-azatricyclo[3.3.1.1³,⁷]dec-4-yl)-amide;
2,2'-bithiophene-5-carboxylic acid (4r)-(1-azatricyclo[3.3.1.1³,⁷]dec-4-yl)-amide;
2,2'-bithiophene-5-carboxylic acid (4s)-(1-azatricyclo[3.3.1.1³,⁷]dec-4-yl)-amide;
5-(3-trifluoromethylphenyl)-furan-2-carboxylic acid (4r)-(1-azatricyclo[3.3.1.1³,⁷]dec-4-yl)-amide;
5-(3-trifluoromethylphenyl)-furan-2-carboxylic acid (4s)-(1-azatricyclo[3.3.1.1³,⁷]dec-4-yl)-amide;
5-(2-nitrophenyl)-furan-2-carboxylic acid (4r)-(1-azatricyclo[3.3.1.1³,⁷]dec-4-yl)-amide;
5-(2-nitrophenyl)-furan-2-carboxylic acid (4s)-(1-azatricyclo[3.3.1.1³,⁷]dec-4-yl)-amide;
2-(pyridin-4-yl)-thiazole-2-carboxylic acid (4r)-(1-azatricyclo[3.3.1.1³,⁷]dec-4-yl)-amide;
2-(pyridin-4-yl)-thiazole-2-carboxylic acid (4s)-(1-azatricyclo[3.3.1.1³,⁷]dec-4-yl)-amide;
2-(thiophen-2-yl)-thiazole-4-carboxylic acid (4r)-(1-azatricyclo[3.3.1.1³,⁷]dec-4-yl)-amide;
5-(thiophen-2-yl)-1H-pyrazole-3-carboxylic acid (4r)-(1-azatricyclo[3.3.1.1³,⁷]dec-4-yl)-amide;
N-[(4r)-1-azatricyclo[3.3.1.1³,⁷]dec-4-yl]-4-(thiophen-2-yl)-benzamide;
N-[(4s)-1-azatricyclo[3.3.1.1³,⁷]dec-4-yl]-4-(thiophen-2-yl)-benzamide;
5-(2-methylthiazol-4-yl)thiophene-2-carboxylic acid (4r)-(1-azatricyclo[3.3.1.1³,⁷]dec-4-yl)-amide; and
3-(thiophen-2-yl)benzoic acid (4r)-(1-azatricyclo[3.3.1.1³,⁷]dec-4-yl)-amide;
or a pharmaceutically acceptable salt thereof.

\* \* \* \* \*

UNITED STATES PATENT AND TRADEMARK OFFICE
CERTIFICATE OF CORRECTION

PATENT NO. : 8,586,746 B2
APPLICATION NO. : 13/012130
DATED : November 19, 2013
INVENTOR(S) : Schrimpf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 202 days.

Page 1 of 1

Signed and Sealed this
Seventh Day of April, 2015

Michelle K. Lee
*Director of the United States Patent and Trademark Office*